US006504892B1

(12) United States Patent
Ning

(10) Patent No.: US 6,504,892 B1
(45) Date of Patent: Jan. 7, 2003

(54) SYSTEM AND METHOD FOR CONE BEAM VOLUME COMPUTED TOMOGRAPHY USING CIRCLE-PLUS-MULTIPLE-ARC ORBIT

(75) Inventor: Ruola Ning, Penfield, NY (US)

(73) Assignee: University of Rochester, Rochester, NY (US)

( * ) Notice: Subject to any disclaimer, the term of this patent is extended or adjusted under 35 U.S.C. 154(b) by 132 days.

(21) Appl. No.: 09/689,847

(22) Filed: Oct. 13, 2000

(51) Int. Cl.$^7$ ................................................ A61B 6/03
(52) U.S. Cl. .............................. 378/4; 378/15; 378/901
(58) Field of Search ............................ 378/4, 8, 15, 19, 378/901

(56) References Cited

U.S. PATENT DOCUMENTS

| | | |
|---|---|---|
| 5,170,439 A | 12/1992 | Zeng et al. |
| 5,257,183 A | 10/1993 | Tam |
| 5,262,946 A | 11/1993 | Heuscher |
| 5,278,884 A | 1/1994 | Eberhard et al. ............... 378/4 |
| 5,365,560 A | 11/1994 | Tam ............................... 378/8 |
| 5,390,226 A | 2/1995 | Tam ............................. 378/19 |
| 5,400,255 A | 3/1995 | Hu |
| 5,444,792 A | 8/1995 | Grangeat et al. |
| 5,461,650 A | 10/1995 | Tam ............................... 378/4 |
| 5,481,583 A | 1/1996 | Heuscher ....................... 378/4 |
| 5,517,602 A | 5/1996 | Natarajan |
| 5,671,265 A | 9/1997 | Andress .................... 378/98.11 |
| 5,802,133 A | 9/1998 | Kawai et al. .................. 378/4 |
| 5,999,587 A | 12/1999 | Ning et al. .................... 378/4 |
| 6,075,836 A | 6/2000 | Ning ....................... 378/98.12 |
| 6,078,638 A | 6/2000 | Sauer et al. .................... 378/4 |

OTHER PUBLICATIONS

P. Grangeat, "Mathematical Framework of Cone Beam 3D Reconstruction via the First Derivative of the Radon Transform", *Mathematical Methods in Tomography*, Herman, Lewis, Natterer (eds.), Lecture Notes in Mathematics, No. 1497, pp. 66–97, Spring Verlag (1990).

L.A. Feldkamp et al., "Practical cone–beam algorithm", J. Opt. Soc. Am. A/vol. 1, No. 6, Jun. 1984 pp. 612–619.

Y. Weng et al., A Reconstruction Algorithm for Helical Cone–Beam SPECT, IEEE Transactions on Nuclear Science, vol. 40, No. 4, Aug. 1993, pp. 1092–1101.

Bruce D. Smith, "Image Reconstruction from cone–Beam Projections: Necessary and Sufficient Conditions and Reconstruction Methods" IEEE Transactions on Medical Imaging, vol. M–4, No. 1, Mar. 1985, pp. 14–25.

B. Smith, "Cone–beam tomography: recent advances and a tutorial review", Optical Engineering, vol. 29, No. 5, May 1990, pp. 524–534.

H. Tuy, "An inversion formula for cone–beam reconstruction", SIAM J. Appl. Math, vol. 43, No. 3, Jun. 1983, pp. 546–552.

*Primary Examiner*—David V. Bruce
(74) *Attorney, Agent, or Firm*—Blank Rome Comisky & McCauley LLP

(57) ABSTRACT

Cone beam volume computed tomography (CBVCT) is carried out by taking signals along an orbit having a circle plus two or more arcs. A reconstruction algorithm is provided to add a correction term to the Feldkamp algorithm and to use the arc data to reconstruct data which cannot be recovered from the circle scan. The part of the reconstruction algorithm for the circle orbit uses filtering functions to simplify digital signal processing. The part of the reconstruction algorithm for the arc orbits uses a window function to resolve data redundancy.

42 Claims, 7 Drawing Sheets

SYSTEM AND METHOD FOR CONE BEAM VOLUME COMPUTED TOMOGRAPHY USING CIRCLE-PLUS-MULTIPLE-ARC ORBIT

CROSS-REFERENCE TO RELATED PATENTS AND APPLICATIONS

The applicant is a named co-inventor in U.S. Pat. No. 5,999,587 and the named inventor in U.S. Pat. No. 6,075,836 and co-pending U.S. patent application Ser. Nos. 09/589,115 and 09/640,713, all of which concern subject matter related to the present invention. The disclosures of all of those patents and applications are hereby incorporated by reference in their entireties into the present disclosure.

FIELD OF THE INVENTION

The present invention is directed to a system and method for reconstruction of images from cone beam volume computed tomography (CBVCT) and more particularly to such a system and method in which the data are taken over an orbit having a circle and two or more arcs.

DESCRIPTION OF RELATED ART

Among all possible applications of the Radon transform, computed tomography (CT) applied in 2-D medical and non-destructive test imaging technology may be the one that has achieved the greatest success. Recognizing the demand for saving scan time in the currently available 2-D CT and consequently greatly improving its functionality, the implementation of CBVCT has been investigated for the past two decades.

The intermediate function derived by Grangeat (P. Grangeat, "Mathematical Framework of Cone Beam 3D Reconstruction via the First Derivative of the Radon Transform," *Mathematical Methods in Tomography, Lecture Notes in Mathematics* 1497, G. T. Herman et al, eds., New York: Springer Verlag, 1991, pp. 66–97) establishes a bridge between the projection of a 3-D object and its 3-D Radon transform and is much more numerically tractable than previously known intermediate functions. With the progress in understanding the so-called data sufficiency condition for an exact reconstruction, a few cone beam non-planar scanning orbits, such as dual orthogonal circles, helical, orthogonal circle-and-line, non-orthogonal dual-ellipse, orthogonal circle-plus-arc, and even general vertex path have been proposed. Correspondingly, the analytic algorithms to exactly reconstruct a 3-D object based upon those non-planar scanning orbits have also been presented.

Generally, a cone beam filtered back-projection (FBP) algorithm can make cone beam reconstruction much more computationally efficient and more easily implemented in a multi-processor parallel computing structure. Hence, an FBP cone beam reconstruction algorithm is desirable in practice, and Feldkamp's algorithm (L. A. Feldkamp, L. C. Davis, and J. W. Kress, "Practical cone-beam algorithm," *J. Opt. Soc. Am. A*, Vol. 1, pp. 612–619, 1984) for the circular orbit is the earliest example. Obviously, Feldkamp's algorithm violates the data sufficiency condition, and an accurate reconstruction without intrinsic artifacts is available only in the central plane overlapping the circular orbit plane, so that some accuracy on the off-central planes has to be sacrificed. Although proposed independently, many algorithms of the prior art featured a common structure of shift variant filtering (SVF) followed by cone beam back-projection. Only 1-D ramp filtering is employed in Feldkamp's algorithm, but a cascade of 2-D operations, such as weighting, 2-D projection, differentiation and 2-D back-projection, are involved in the shift variant filtering. The complexity of the SVF ($O(N^4)$) is higher than that of the 1-D ramp filtering of Feldkamp's algorithm ($O(N^3 \log N)$). Another important common feature possessed by many algorithms of the prior art is a normalized redundancy function (NRF) adopted to compensate for the multiple intersections of the projection plane with the source trajectory. Recently, that kind of algorithm has been extended to a more general situation in which an arbitrary vertex path is involved as long as the data sufficiency condition is satisfied. Apparently, the NRF is data-acquisition-orbit-dependent and has discontinuities in data acquisition orbits which meet the data sufficiency condition, but it can be analytically calculated for either a specific data acquisition orbit or even an arbitrary vertex path. On the other hand, the algorithm by Hu (H. Hu, "A new cone beam reconstruction algorithm for the circle-and-line orbit," *Proceedings of International Meeting on Fully 3D Image Reconstruction in Radiology and Nuclear Medicine*, pp. 303–310, 1995; and H. Hu, "Exact regional reconstruction of longitudinally-unbounded objects using the circle-and-line cone beam tomographic system," *Proc. SPIE*, Vol. 3032, pp. 441–444, 1997) for an orthogonal circle-plus-line orbit is promising in saving computation resource, since a window function, instead of the NRF, is employed for the cone beam reconstruction from the projection data acquired along the line orbit.

Due to mechanical feasibility, a circular x-ray source trajectory is still the dominant data acquisition geometry in all commercial 2-D/3-D CT systems currently available. Based upon a circular source trajectory, a number of data acquisition orbits can be implemented by either moving the table or tilting the CT gantry. An orthogonal circle-plus-arc orbit has been presented. It possesses advantages that can not be superseded by other "circle-plus" geometries, especially in the application of image guided interventional procedures requiring intraoperative imaging, in which the movement of a patient table is to be avoided. Further, it can be easily realized on a C-arm-based imaging system, which is being used more and more for tomography in recent years. The orthogonal circle-plus-arc orbit can be realized by acquiring one set of 2-D cone beam circle projections while rotating an x-ray source and a 2D detector on a circular gantry and then acquiring another set of 2-D cone beam arc projections while tilting the gantry along an arc which is orthogonal to and coincident with the circular orbit at the same radius. The exact CBVCT reconstruction algorithm associated with that circle-plus-arc orbit is not in the FBP form. The rebinning process involved in the algorithm requires storage for all information in the Radon space, and makes the CBVCT reconstruction computationally inefficient. Further, the arc sub-orbit provides information covering its Radon sub-domain only once, but the circular sub-orbit provides information covering its Radon sub-domain twice. That unbalanced coverage in the Radon space may result in non-uniformity of noise characteristic in reconstructed images.

A particular application of the present invention is in the detection of lung cancer and other malignancies. CT scanning plays a central role in much of the thoracic imaging used in detection of lung cancer and other malignancies. CT is non-invasive, easy to perform, and usually straightforward to interpret. It is either the primary modality or the referral modality for the detection of pulmonary masses (primary and metastatic), non-invasive staging of primary bronchogenic carcinoma, and for detection of major complications of malignancies, particularly pulmonary emboli, and infections. However, present helical CT has three major technical shortcomings. First, helical CT scans require a long or multiple breath holds for whole lung imaging, depending on slice thickness. Second, slice thickness vs. coverage vs. scan time tradeoff: programming thinner slices increases scan time or decreases coverage. The spatial resolution is not isotropic; through plane resolution is limited by slice thickness and a few times lower than that of in-plane. Third, the clinically achievable in-plane resolution for a large FOV, such as whole lung imaging, is limited and less than or equal to 1.0 lp/mm.

CT of the chest is a potential screening tool for lung carcinoma. While screening programs based on conventional x-rays had poor sensitivity and diagnosed most carcinomas after the window of surgical cure had passed, CT scans reveal nodules below 1 centimeter with higher potential cure rates. A drawback of screening CT is poor specificity. Benign sub-centimeter nodules are common (non-calcified granulomas, intrapulmonary lymph nodes, focal regions of atelectasis). The best diagnostic algorithm post-discovery of sub-centimeter nodules is unclear. Universal resection seems impractical. Potential diagnostic algorithms include evaluating the nodule enhancement, border characteristics, and growth. In all of these cases, accurate depiction of a small nodule is necessary. Helical CT, while readily detecting these nodules, has partial volume averaging problems in accurate characterization. It would therefore be desirable to provide a scanning system and method with sub-millimeter isotropic resolution, which would potentially better characterize the density and size of these small nodules. Accurate size measurement would allow short-term follow-up to evaluate for growth.

While CT screening for bronchogenic carcinoma in the high-risk population may or may not be clinically beneficial and economically practical, chest CT for the detection of metastases is commonly performed. CT is performed at the time of initial diagnosis, as interval monitoring for detection of disease, and as follow-up of detected nodules which are not initially resected. In all cases, improved detection and characterization, particularly that of interval growth, should be clinically beneficial.

Three image intensifier (II)-based cone beam reconstructions for volume lung imaging have been reported before. However, all II-based CBVCT for volume lung imaging suffers from inaccurate reconstruction due to the use of a single circle cone beam acquisition geometry and its corresponding approximating algorithm by Feldkamp et al, in addition to a limited performance of the II-CCD imaging chain. The best low contrast detectability of the II-based cone beam CT for volume lung imaging is 10 HUs for a 3 mm object.

SUMMARY OF THE INVENTION

It will be readily apparent from the above that a need exists in the art to overcome the above-noted limitations of the prior art. It is therefore an object of the invention to satisfy the data sufficiency condition while achieving a more balanced coverage. It is another object of the invention to do so in a computationally efficient manner which can be adapted to parallel cone beam reconstruction.

To achieve the above and other objects, the present invention is directed to a system and method for reconstructing images from data taken over a circle and two or more arcs. An FBP reconstruction algorithm is presented for reconstructing the images.

The efficiency of reconstruction is critical for the application of CBVCT in the image-guided interventional procedures, and the reconstructed images with uniform noise characteristic are desired in practice. In order to overcome the previously mentioned shortcomings of the circle-plus-arc orbit and its associated Radon Transform-based reconstruction algorithm, a circle-plus-two-arc orbit and an analytic FBP cone bean reconstruction algorithm are used. The result given by Hu for the circular cone beam projections is directly incorporated. For the cone beam projections acquired along the arc orbits (namely, arc cone beam projections), originating from the equation established by Grangeat and the inverse Radon transform, an analytic reconstruction solution is obtained. That solution is different from known solutions because a window function, instead of an NRF, is employed to compensate for the multiple intersections of the projection plane with the x-ray source trajectory. Since its support in the Radon domain is very limited, the window function of the present invention significantly reduces the computational cost of the reconstruction from the arc CB projections.

Most objects to be reconstructed in medical or non-destructive x-ray CT are longitudinally unbounded. Hence, a cone beam reconstruction algorithm should address such a truncation problem. In order to solve the so-called truncated cone beam projection, several methods have been proposed. It has been demonstrated that a finite region of interest (ROI), for which the extended data sufficiency condition is satisfied, can be reconstructed accurately, although that finite ROI is slightly smaller than the ROI which can be scanned by a detector. The circle-plus-two-arc orbit and its associated cone beam FBP reconstruction algorithm in the present invention are intrinsically capable of dealing with the truncation problem, and its thorough evaluation is accomplished herein.

The circle-plus-arcs orbit possesses advantages over other "circle-plus" orbits for the application of x-ray CBVCT in image-guided interventional procedures requiring intraoperative imaging, in which movement of the patient table is to be avoided. A cone beam circle-plus-two-arc orbit satisfying the data sufficiency condition and a filtered back-projection (FBP) algorithm to reconstruct longitudinally unbounded objects is presented here. In the circle sub-orbit, the algorithm employs Feldkamp's formula and another FBP implementation. In the arc sub-orbits, an FBP solution is obtained originating from Grangeat's formula, and the reconstruction computation is significantly reduced using a window function to exclude redundancy in Radon domain. The algorithm's merits include the following: Only 1-D filtering is implemented even in a 3-D reconstruction, only separable 2-D interpolation is required to accomplish the 3-D back projection, and the algorithm structure is appropriate for parallel computation.

The present invention has the following characteristics and advantages. A flat panel detector (FPD) can be used. The invention can incorporate scattering correction and volume-of-interest (VOI) reconstruction. The present invention can be used for medical imaging, nondestructive testing or any other purpose in which such imaging is desired.

In the reconstruction algorithm of the preferred embodiment, all the components are in a filtered backprojection format. That reconstruction algorithm is more computationally efficient than those of the prior art and is ready for parallel cone beam reconstruction. That algorithm can be used to provide an exact reconstruction of a longitudinally unbounded object. The CBVCT reconstruction of the preferred embodiment is the 3D matrix of attenuation coefficient distribution of a 3D object.

In the present invention, the data are taken through a scan such as a quasi-spiral scan. To achieve the fastest scan, a simplified scan, such as only tilt in plus circle scan, can be used to satisfy the data sufficiency condition. The second set of arc projection scans (gantry tilt-out scans) is optional to improve image quality. The total acquisition time can be reduced by decreasing the sampling rate on the arcs or by using only a gantry-tilt-in plus a circle scan during the quasi-spiral scan.

The present invention offers the following particular advantages when used to detect lung cancer. First, the present invention requires a much shorter volume scanning time relative to helical CT. In a single volume scan, an entire acquisition can be performed. The present invention can improve acquisition efficiency by a factor of 25 for 1 mm slice thickness per volume scan vs. a single ring helical CT. Assuming a 25 cm segment to be scanned for a whole lung imaging and 1 mm/slice, the present invention can be at least 24 times faster than a single ring detector helical CT and 3 (for gantries with 0.5 sec./revolution) to 6 times faster than a multi-ring detector helical CT. The fast volume scan eliminates the respiratory misregistration problems, such as those caused by the requirement that the patient hold his or her breath, and is less sensitive to patient motion.

Second, the present invention can provide isotropic resolution in the x, y and z directions and provide true 3D reconstruction images. The spatial resolution of FPD-based CBVCT is limited by the fineness of our detector array, not by collimation. An FPD-based CBVCT achieves spatial resolution on the order of 1–2 lp/mm in routine mode. The present invention can provide higher resolution in all three directions than a helical CT.

Third, the embodiment with ultra-high resolution VOI reconstruction can provide true 3D tomographic reconstruction with spatial resolution approaching that of screen-film projection imaging, but with 50–100 times better contrast resolution than projection imaging. This spatial resolution capability cannot be achieved in any current helical CT.

In addition, the present invention can more efficiently use x-ray tube output and greatly reduce the tube loading requirement. This will reduce the manufacture cost of CT tubes because a very heavy duty and very costly x-ray CT tube ($60,000–$100,000/tube) may not be needed, and/or the operating cost because the life of a CT tube will be many times longer.

The present invention thus improves the sensitivity and specificity of lung cancer detection as well as other types of cancer detection. In addition, it will highly significant to the early detection and management, not only of lung cancer, but also of other malignancies.

There are several radiological or biological characteristics of carcinoma that can be imaged. First, carcinoma has different x-ray linear attenuation coefficients from surrounding tissues. Second, carcinoma has a substantially higher volume growth rate compared to a benign tumor, which lacks growth. Third, carcinoma has border patterns distinguishable from those of a benign tumor. Fourth, benign tumors show different contrast enhancement after intravenous contrast injection. Fifth, the presence of neovascularity can indicate cancer. Conventional cancer detection techniques such as chest projection imaging rely mainly on the first characteristic and partially use the third characteristic for cancer detection. Since mammography is a two-dimensional static imaging technique, it cannot provide any information regarding characteristics 2, 4, or 5. The present invention, by allowing fast scans and permitting the use of contrast injection if desired, can be used to detect cancers in accordance with all five characteristics.

CT scanning is a key modality for detecting pulmonary malignancies. It can detect lesions as small 2-mm diameter. It is, however, imperfect for detection of nodules for the following reasons:

Nodules may not be imaged if the lungs cannot be scanned in a single breathhold. Respiratory misregistration occurs when a CT scan of the lungs is acquired in several different breath holds. Because patients do not reliably hold their breath in the same phase of respiration, and because pulmonary lesions move cranially or caudally with respiration, a CT scan composed of slices obtained from different breath holds may fail to detect a lesion because that lesion was never imaged. The present invention permits scanning the entire lungs in a single breathhold and thus can eliminate this source of detection error.

Nodules may be present on the CT images but fail to be recognized by the interpreting radiologist. A retrospective review of nine patients with missed lung cancer on CT found five missed tumors that were peripheral and <3 mm in diameter and four central tumors measuring up to 8 mm in diameter. These small peripheral nodules were likely not seen while the larger central nodules were not recognized set against the background of the larger complex branching vessels. Review of a CT dataset electronically, and in planes other than the axial plane might also prove to have further increase in sensitivity for nodule detection. The present invention provides the first system capable of scanning the entire chest with sub-millimeter isotropic resolution. Isotropic resolution with sub-millimeter resolution in all directions would be ideally suited for electronic interpretation in axial, oblique, coronal and sagittal planes.

Partial volume averaging with adjacent lung can make small pulmonary nodules difficult or impossible to detect by helical CT. Helical CT of canine metastatic osteosaroma found 44% of metastases $\leq 5$ mm vs. 91% of metastases >5 mm. Usually, helical CT reconstructs images at an interval approximately equal to the collimation, 5–7 mm. Some clinically relevant nodules are smaller than the slice thickness. Reconstructing images at a smaller reconstruction interval increases the sensitivity for lung nodule detection. This is due to the non-linear slice sensitivity profile of helical CT reconstruction. These overlapping reconstructions have a better chance of placing small nodules in the center of the slice where they will be displayed with higher density and be more easily seen. The present invention can overcome this problem because slices at <1 mm thick would essentially eliminate partial volume averaging and also assure that a nodule larger than 3 mm would have a slice through its approximate center.

Nodule size is difficult to measure accurately by helical CT. The apparent size of a pulmonary nodule depends on the thickness of the slice and where the slice is reconstructed relative to the nodule. Accurate size measurements of the nodules are necessary to detect small amounts of growth in short-term follow-ups. A 3 mm diameter nodule growing to 4 mm diameter has more than doubled in volume. Because the detection of small nodules is becoming increasingly common due to helical CT, it is likely that imaging algorithms will need to incorporate follow-up of small nodules for growth. Accurate sizing would be essential. CBVCT will provide 0.125–0.7 mm voxel size and will allow accurate measurements of nodule size and nodule volume.

Small nodule density (attenuation coefficient) is difficult to measure accurately by helical CT. The apparent density of a pulmonary nodule in helical CT depends on the position of the nodule relative to the position of the reconstructed slice. The relative movement of the slice by one or two mm may make a calcified nodule appear non-calcified. For nodules smaller than the slice thickness (routinely 5–10 mm in helical CT), there is partial volume averaging of the nodule with adjacent air and an accurate density can not be determined. The nodule density is useful for characterization in two major respects. One is the detection of calcification indicating benignity. The second is that malignant pulmonary nodules appear to have more rapid contrast enhancement than benign nodules. Sub-millimeter thick slices, achieved by CBVCT, will allow accurate density measurements of small nodules without partial volume averaging and without necessity for post-processed overlapping reconstructions. This should better detect calcification, and more accurately characterize the amount of enhancement.

Fine spiculations and other nodule border characteristics are best determined with high resolution CT. On helical CT scanners, this requires locating the nodule prospectively, as it is impractical to acquire high-resolution CT 1-mm thick slices throughout the entire lungs. CBVCT would acquire high-resolution images through every nodule without prior knowledge of its location or the need for technologists or physician localization during the scan. The ultra-high resolution VOI reconstruction mode of CBVCT will provide even higher resolution for target imaging after the survey lung imaging of CBVCT with lower resolution. This mode may be even more useful for characterizing nodule border. The value of universal high resolution CT for characterizing benign vs. malignant nodules may also prove beneficial.

A particular implementation of CBVCT provides high contrast resolution of 0.7–4 lp/mm, and low contrast detectability of 3–5 CT number within a short breath hold (2–8 seconds). Such an implementation preferably includes an appropriate 2D detector system which has a high detection quantum efficiency (DQE), high dynamic range, high spatial resolution, minimal geometric distortion, and which is capable of high image acquisition rates with little image lag and excellent linearity. It also preferably includes a data acquisition scheme that will result in a complete set of projection data with little additional mechanical complexity. This provides an exact cone beam reconstruction algorithm which is based on the complete set of data, thereby permitting imaging in a large FOV (for example 14"–16"). A third aspect which is preferably included is x-ray scatter control and correction techniques to further improve low contrast detectability.

The present invention expands the application of CBVCT from angiography to volume lung imaging and other applications that require soft tissue differentiation. CBVCT can potentially be applied to pulmonary emboli detection, liver cancer detection, volumetric brain perfusion, diagnosis of acute stroke, and colon cancer detection, etc.

For lung cancer and other malignancies, the present invention has application to malignancy detection, monitoring, management and treatment and in particular to the development of treatment plans.

BRIEF DESCRIPTION OF THE DRAWINGS

A preferred embodiment of the present invention will be set forth in detail with reference to the drawings, in which.

DETAILED DESCRIPTION OF THE PREFERRED EMBODIMENT

A preferred embodiment of the present invention will now be set forth in detail with reference to the drawings. First, the reconstruction algorithm will be derived. Second, a device on which the reconstruction algorithm can be implemented will be shown.

Figure 1:
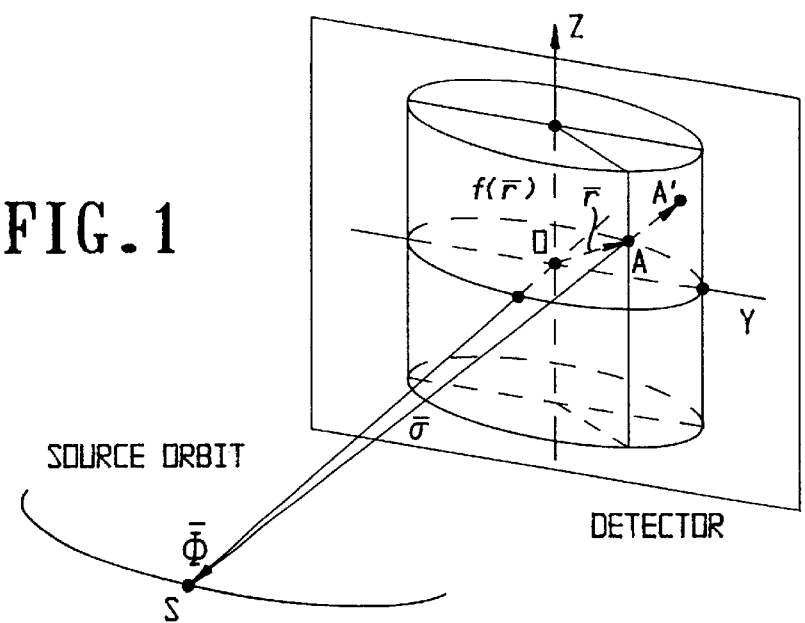
FIG. 1 is a schematic drawing showing a cone-beam projection.

The cone beam projection of a 3-D object is schematically illustrated in FIG. 1, where o is the origin of the coordinate of the real 3-D space $R^3$, upon which the algorithm is derived. Y and Z are the local axes in the plane of the virtual detector. $\vec{OS} = \vec{\Phi}$ is the vector which represents the cone beam focal point S, and point A' is the projection on the detector plane of A, which is a point within the 3-D object to be reconstructed, along the unit directional vector $$\vec{\sigma} = \frac{\vec{SA}}{|\vec{SA}|}. \tag{1}$$

The vector from O to A is $\vec{r}$. The cone beam projection of the 3-D object $f(\vec{r})$ is defined as:

$$g(\vec{\Phi}, \vec{\sigma}) = \int_{-\infty}^{\infty} f(\vec{\Phi} + t\vec{\sigma}) dt \tag{2}$$

The reconstruction algorithm is derived for a longitudinally bounded object first, and its is capability of regionally reconstructing a longitudinally unbounded object will be analyzed in detail later. Since most objects to be reconstructed in medical and non-destructive test tomography are cylinder-like, the 3-D object to be reconstructed is assumed to be a cylinder whose half height is represented by h, and radius by R.

Figure 2:
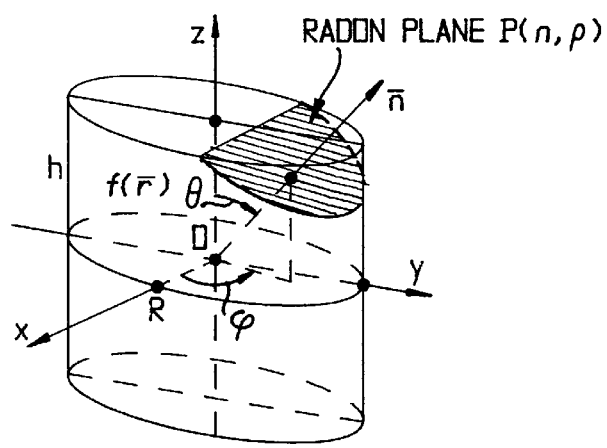
FIG. 2 is a schematic drawing showing a Radon plane.

The definition of a 3-D Radon plane $P(\vec{n}, \rho)$ is schematically illustrated in FIG. 2, where $$\vec{n} = (\sin\theta \cos\phi, \sin\theta \sin\phi, \cos\theta) \tag{3}$$

is the normal vector, and ρ the distance away from the coordinate origin O. In 3-D Cartesian coordinates, any plane can be uniquely identified by a normal vector and a distance away from O and is the set of all points for which $$\vec{r} \cdot \vec{n} - \rho = 0. \tag{4}$$

Recognizing the existence of several versions of the data sufficiency condition, the preferred embodiment uses the one which can be the most simply expressed: All planes passing through the object to be reconstructed must contain a point in the scanning orbit. Obviously, a circular orbit, which is the simplest in practice for 3-D reconstruction, violates the data sufficiency condition in a way demonstrated in FIG. 3, i.e., the Radon transform of the circular CB projections provide no coverage on the shadowed sub-domain in the Radon space. In the perspective of inverse Radon transform, the sub-domain missed in the Radon space by the circular orbit (namely missed Radon sub-domain) has to be covered by additional non-circular orbits.

The requirement for the circle-plus-one-arc orbit to meet the data sufficiency condition and cover the 3-D cylinder object to be reconstructed completely is known in the art to be (see FIG. 4A):

$$D \geq \sqrt{2} R \tag{5}$$

$$\lambda_{min\_s} = 2\tan^{-1}\left(\frac{h}{D-R}\right) \tag{6}$$

where R is the radius of the cylinder object to be reconstructed, D is the radius of the arc orbits, and $\lambda_{min_{1,3}s}$ is the minimum arc spanning angle range of the whole single arc.

Figure 4A:
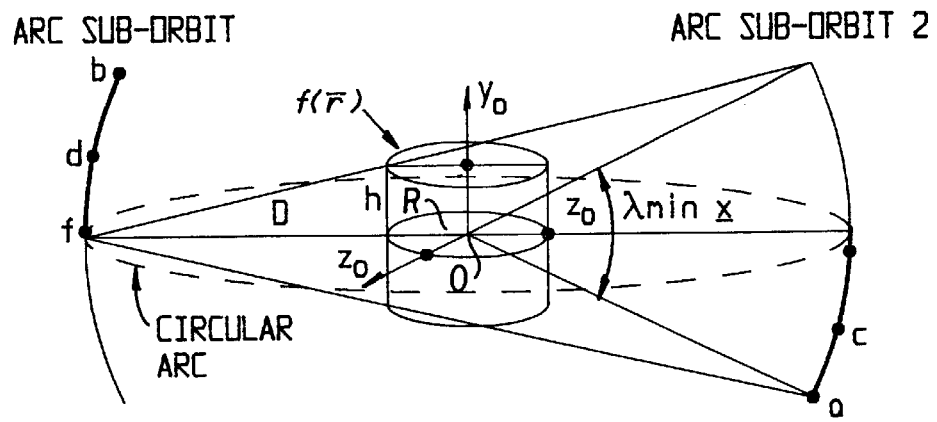
FIG. 4A is a schematic diagram showing the ability of the circle-plus-two-arc orbit to satisfy the data sufficiency condition.

Since an uneven sampling is achieved by the circle-plus-arc orbit in the missed Radon sub-domain, some artifacts may occur in reconstructed images. Further, the arc sub-orbit is in odd-symmetry in the plane determined by itself. Such an odd-symmetry makes the non-uniformity of the sampling in Radon space worse, and may result in more reconstruction artifacts. On the other hand, the redundancy function equals 1 within the missed sub-domain in the Radon space, while the redundancy function equals 2 within the sub-domain covered by the circular data acquisition orbit. In the perspective of signal processing, that kind of difference in the redundancy function results in an uneven noise characteristic in reconstructed images. To avoid the artifacts caused by the odd-symmetry and maintain identical Radon information redundancy between the sub-domains covered by the circular and arc orbits respectively, a circle-plus-two-arc orbit is used in the preferred embodiment, although the invention could be adapted for a circle plus more than two arc orbits. As schematically shown in FIG. 4A, the circle-plus-two-arc orbit consists of a circle and a pair of arcs. One is called arc sub-orbit 1 and is represented by the solid curves; the other is called arc sub-orbit 2 and is represented by the dashed curves. The arc sub-orbit plane is perpendicular to the circular sub-orbit plane, and they are concentric at point O with the same radius D. It is noticed that an even-symmetry is achieved by integrating arc sub-orbit 1 and arc sub-orbit 2 in the arc sub-orbit plane $(x_o, y_o)$.

In the fixed coordinate system $(x_o, y_o, z_o)$ illustrated in FIG. 4A, the circle-plus-two-arc orbit can be analytically depicted as $$\begin{cases} \phi_c(\lambda) = (D\cos\lambda, \ 0, \ -D\sin\lambda) \\ \lambda \in \Lambda_c = [\ 0, \ 2\pi\ ] \end{cases} \tag{7}$$

$$\begin{cases} \phi_{a_1}(\lambda) = (D\cos\lambda, \ D\sin\lambda, \ 0) \\ \lambda \in \Lambda_{a_1} = [\ -\lambda_{min\_d}, \ 0\ ] \cup [\ \pi - \lambda_{min\_d}, \ \pi\ ] \end{cases} \tag{8}$$

$$\begin{cases} \phi_{a_2}(\lambda) = (D\cos\lambda, \ D\sin\lambda, \ 0) \\ \lambda \in \Lambda_{a_2} = [\ 0, \ \lambda_{min\_d}\ ] \cup [\ \pi, \ \pi + \lambda_{min\_d}\ ] \end{cases} \tag{9}$$

where $\phi_a(\lambda)$ represents the circle sub-orbit, and $\phi_{a_1}(\lambda)$ the arc sub-orbit 1, and $\phi_{a_2}(\lambda)$ the arc sub-orbit 2, respectively. Theoretically, the minimum cone angle for each arc in the circle-plus-two-arc orbit is cut down to half that required by the single arc in the circle-plus-one-arc orbit $$\lambda_{min\_d} = \frac{1}{2}\lambda_{min\_s} = \tan^{-1}\left(\frac{h}{D-R}\right) \tag{10}$$

Accordingly, the reconstruction algorithm can be most broadly expressed as $$f(\vec{r}) = f_c(\vec{r}) + f_a(\vec{r}) \tag{11}$$

where $f_c(\vec{r})$ is the component reconstructed from the sub-domain in the Radon domain support corresponding to the circular cone beam projections, and $f_a(\vec{r})$ the component of the arc cone beam projections.

Figure 5:
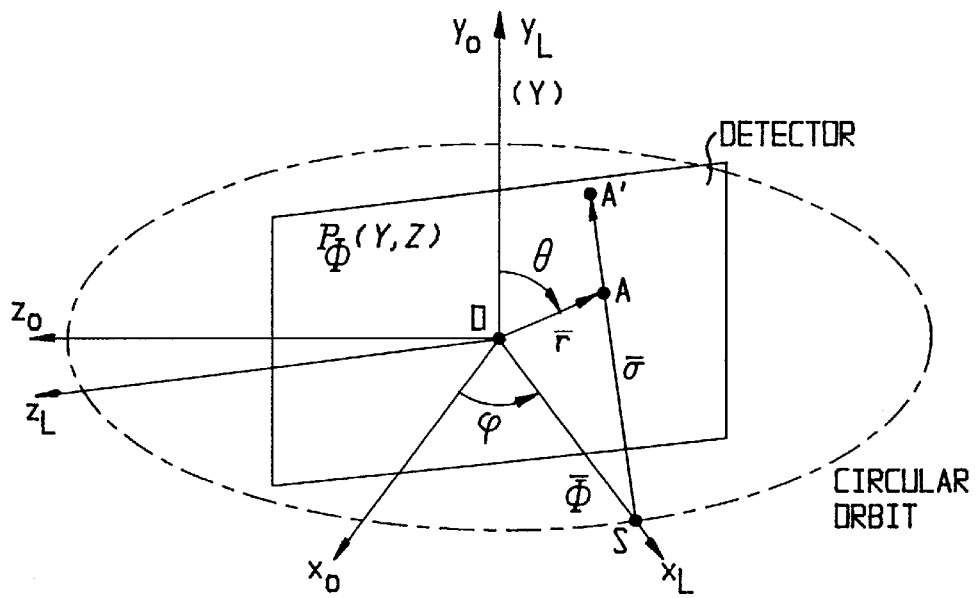
FIG. 5 is a schematic diagram showing the coordinate system and parameters used in the reconstruction of the circular projection.

The coordinate system on which the reconstruction algorithm for the circular cone beam projections is derived is illustrated in FIG. 5. $(x_L, y_L, z_L)$ is the local coordinate system which rotates rigidly in phase with the detector. $\vec{r}$ represents a vector that determines a point A within the 3-D object to be reconstructed, and (Y,Z) is the coordinate of the projection of A in the detector coordinate system. The circular sub-orbit is within the plane determined by $(z_o, x_o)$, and $P_\Phi(Y,Z)$ is the cone beam projection with the source focal point at $\vec{\Phi}$.

It has been shown that $f_c(\vec{r})$ can be further split into:

$$f_c(\vec{r}) = f_{c_1}(\vec{r}) + f_{c_2}(\vec{r}) \tag{12}$$

$f_{c_1}(\vec{r})$ corresponds to the FDK algorithm and can be obtained using the following formulae that are modified to match the coordinate system shown in FIG. 5:

$$f_{c_1}(\vec{r}) = \frac{1}{4\pi^2} \oint_{[0,2\pi]} d\Phi \frac{D^2}{(D - \vec{r} \cdot \vec{x}_L)^2} P'_\Phi(Y(\vec{r}), Z(\vec{r})) \tag{13}$$

$$Y(\vec{r}) = \vec{r} \cdot y_L \frac{D}{D - \vec{r} \cdot \vec{x}_L}, \quad Z(\vec{r}) = \vec{r} \cdot z_L \frac{D}{D - \vec{r} \cdot \vec{x}_L} \tag{14}$$

$$P'_\Phi(Y, Z) = \int_{-\infty}^{\infty} dz h_{\omega'}(Z - z) \hat{P}_\Phi(Y, z) \tag{15}$$

$$\hat{P}_\Phi(Y, Z) = \frac{D}{(D^2 + Y^2 + Z^2)^{\frac{1}{2}}} P_\Phi(Y, Z) \tag{16}$$

$$h_{|\omega|}(Z) = \int_{-\omega_0}^{\omega_0} |\omega| d\omega \exp(j\omega Z) \tag{17}$$

where $\omega_0$ is the integral limit, which is determined by the spatial sampling frequency of the detector, in the Fourier domain.

On the other hand, $f_{c_2}(\vec{r})$ can be obtained using the following formulae that are also modified to match the coordinate system shown in FIG. 5:

$$f_{c_2}(\vec{r}) = -\frac{1}{4\pi^2} \oint_{[0,2\pi]} d\Phi \frac{y_L}{(D - \vec{r} \cdot x_L)^2} P'_\Phi(Y(\vec{r})) \quad (18)$$

$$Y(\vec{r}) = \vec{r} \cdot y_L \frac{D}{D - \vec{r} \cdot x_L} \quad (19)$$

$$P'_\Phi(Y) = \frac{\partial}{\partial Y}\sigma_\Phi(Y) = \int_{-\infty}^{\infty} h_{j\omega}(Y - y)\sigma_\Phi(Y)dy \quad (20)$$

$$\sigma_\Phi(Y) = \int_{-L_z}^{L_z} \hat{P}_\Phi(Y, z)dz \quad (21)$$

$$\hat{P}_\Phi(Y, Z) = \frac{D}{(D^2 + Y^2 + Z^2)^{\frac{1}{2}}} P_\Phi(Y, Z) \quad (22)$$

$$h_{j\omega}(Y) = \int_{-\omega_0}^{\omega_0} j\omega \exp(j\omega Y)d\omega \quad (23)$$

where $L_z$ is the integral limit along the Z direction, and $\omega_0$ is the same as that in (17).

Both (13) and (18) are in the FBP form, and reconstruction from the circular cone beam projections is computationally efficient because only 1-D filters $h_{j\omega}(z)$ and $h_{j\omega}(y)$ are involved in the filtering process. In the digital signal processing point of view, $$h_{|\omega|}(n) = \begin{cases} \frac{1}{4} & n = 0 \\ -\frac{1-(-1)^n}{8\pi^2}\frac{1}{n^2} & n \neq 0 \end{cases} \quad (24)$$

and $$h_{j\omega}(n) = \begin{cases} 0 & n = 0 \\ (-1)^n \frac{1}{n} & n \neq 0 \end{cases} \quad (25)$$

In order to reduce numerical artifact and constrain noise, a Hamming window is implemented while filtering.

It is known that the Radon transform of the circular CB projections fulfills only a torus in the 3-D Radon domain. As argued by Hu, the assumption that the redundancy function equals 2 is valid only for the Radon domain point inside the torus. With respect to the Radon domain point on the boundary of the torus, which corresponds to the tangential intersection of the projection plane with the circular orbit in the spatial domain, the redundancy function equals 1. Hence, the reconstruction implemented using Feldkamp's algorithm takes only the contribution from the Radon domain point inside the torus. In order to take the contribution from the Radon domain point on the boundary of the torus into account, the complementary term $f_{c_2}(\vec{r})$ should be incorporated into the algorithm to implement the reconstruction from circular cone beam projections.

As elucidated above, employing the arc sub-orbits provides information in the Radon domain to cover the missed Radon sub-domain. Considering computational efficiency, a reconstruction algorithm for the arc cone beam projections in the FBP form is desired in practice.

Figure 6:
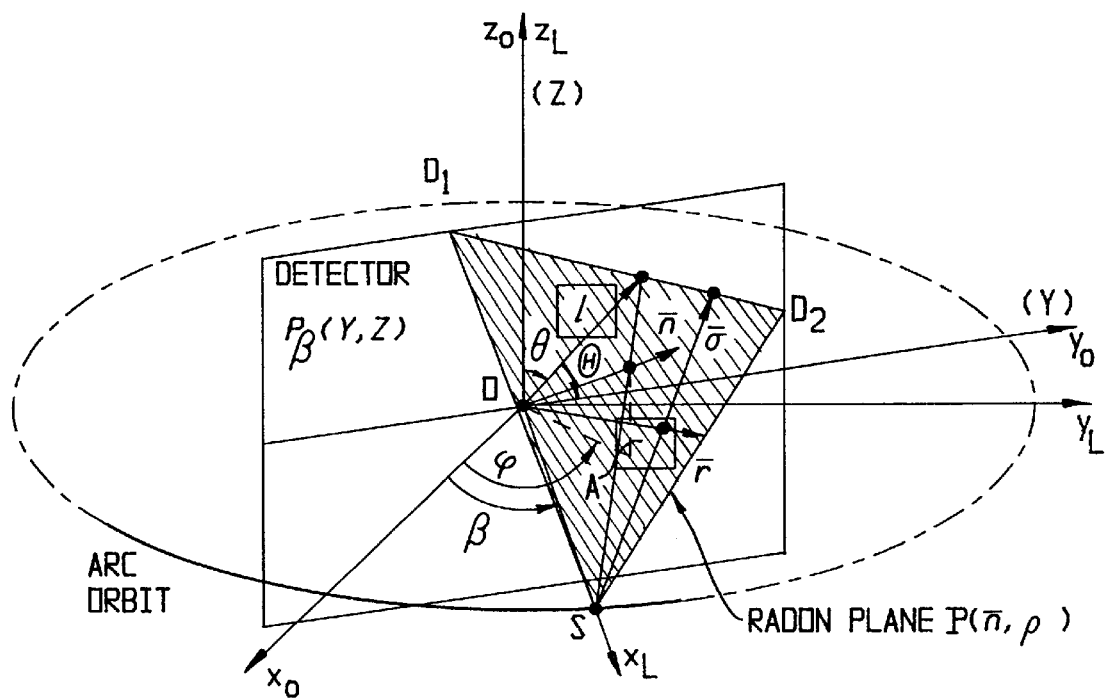
FIG. 6 is a schematic diagram showing the coordinate system and parameters used in the reconstruction of the arc projections.

Before the transform itself is presented, some variables will be defined with reference to FIG. 6. The Radon plane containing S and A intersects the detector to define a line segment having end points $D_1$ and $D_2$. The point of closest approach of that line segment to O is at a point C. The line segment connecting O to C has a length $\Theta$ and defines an angle $\Theta$ with the $y_L$ axis. The origin S of the cone beam is along one of the arc orbits at an angle $\beta$ from the $x_o$ axis.

The 3-D Radon transform and its inverse of the object $f(\vec{r})$ are defined respectively as:

$$R(\vec{n}, \rho) = \int_{-\infty}^{\infty} f(\vec{r})\delta(\vec{r} \cdot \vec{n} - \rho)d\vec{r} \quad (26)$$

$$f(\vec{r}) = -\frac{1}{4\pi^2} \int_0^{\pi} \int_{-\frac{\pi}{2}}^{\frac{\pi}{2}} d\varphi d\theta \sin\theta \frac{\partial^2}{\partial \rho^2} R(\vec{n}, \rho)\bigg|_{\rho=\vec{r}\cdot\vec{n}} \quad (27)$$

Based upon the geometry shown in FIG. 6 and originating from the equation established by Grangeat and the inverse Radon transform in Equation (27), the reconstruction algorithm for the arc CB projections can be written as (see APPENDIX A)

$$f_a(\vec{r}) = 0.5 \cdot f_{a_1}(\vec{r}) + 0.5 \cdot f_{a_2}(\vec{r}) \quad (28)$$

where the factor 0.5 is to compensate for the data redundancy resulting from the double coverage on the missed sub-domain in the Radon domain by the two arc sub-orbits, and $f_{a_i}(\vec{r})$ (i={1,2}) can be expressed in the FBP form:

$$f_{a_i}(\vec{r}) = -\frac{1}{4\pi^2} \int_{-\beta_i}^{\beta_i} \int_{-\frac{\pi}{2}}^{\frac{\pi}{2}} P_{a_i}(\beta, l, \Theta) d\Theta d\beta \quad (29)$$

$$P_{a_i}(\beta, l, \Theta) = \frac{D^2 + l^2}{D^2} w(\beta, l, \Theta) \cos\Theta \left[ \frac{2l}{D^2} \frac{\partial}{\partial l} + \frac{D^2 + l^2}{D^2} \frac{\partial^2}{\partial l^2} \right] I_i(\beta, l, \Theta) \quad (30)$$

$$I_i(\beta, l, \Theta) = \int_{-Z_i}^{Z_i} \int_{-Y_i}^{Y_i} P_{\beta,i}(Y, Z)\delta(Y\sin\Theta + Z\cos\Theta - l)dYdZ \quad (31)$$

$$Y(\vec{r}) = \vec{r} \cdot y_L \frac{D}{D - \vec{r} \cdot x_L} \quad \text{and} \quad Z(\vec{r}) = \vec{r} \cdot z_L \frac{D}{D - \vec{r} \cdot x_L} \quad (32)$$

where $\vec{r}$ represents a vector that determines a point A within the 3-D object to be reconstructed, (Y,Z) is the coordinate of the projection of A in the detector coordinate system, $Y_i$ and $Z_i$ are the integral limits along Y and Z axes respectively, $P_{\beta,i}(Y,Z)$ (i={1,2}) is the cone beam projection at angle $\beta$ along the arc orbits, and $$w(\beta, l, \Theta) = \begin{cases} 1 & l\sin\beta > D \cdot (1 - \cos\Theta\cos\beta) \\ 1 & l\sin\beta < -D \cdot (1 + \cos\Theta\cos\beta) \\ 0 & \text{elsewhere} \end{cases} \quad (33)$$

is the window function derived in Appendix B to resolve the data redundancy and constrain the back-projection for the arc cone beam projections. The support of the window function $w(\beta,l,\Theta)$ in the sinogram domain is very limited, and the computational resources for the reconstruction from the arc cone beam projections can be saved substantially. Both the $1^{st}$ and $2^{nd}$ derivative of the sinogram along the distance direction are obtained using the 1-D linear digital operator $h_{j\omega}(n)$.

Notice that the algorithm structure of Equations (29)–(33) look similar to the algorithm presented by Hu. However, there are important differences between the derivation of Equations (29)–(33) and that in the prior art. First, each source point defines a sphere in the Radon domain (namely the Radon sphere), and the diameter of a Radon sphere is determined by the distance between the source point and the origin of the coordinate system. The diameters of the Radon spheres along the arc sub-orbits in that algorithm are constant, but those along the line sub-orbit are variable. With respect to the FBP CBVCT reconstruction, a series of Radon spheres with identical diameter will sample the missed Radon sub-domain more uniformly than a series of Radon spheres with varying diameters. It is possible for a more uniform sampling in the missed Radon sub-domain to create less artifacts in the FBP cone beam reconstruction. Second, the window function (33) is distinct from that in the prior art.

The capability of regionally reconstructing a longitudinally unbounded object is essential for the application of CBVCT in medical or non-destructive test imaging, since most objects to be reconstructed in practice are longitudinally unbounded (that is also called the truncation problem). The circle-plus-two-arc orbit satisfies the extended data sufficiency condition proposed by Kudo and Saito (H. Kudo and T. Saito, "An extended completeness condition for exact cone-beam reconstruction and its application," *IEEE Conf Rec. 1994 Nuclear Science and Medical Imaging Symposium*, Norfolk, Virginia, pp. 1710–1714, 1995). Consequently, its associated cone beam FBP reconstruction algorithm presented above addresses the truncation problem by employing the window function $w(\beta,l,\Theta)$, even though the object to be reconstructed is assumed longitudinally bounded in its derivation. That means that an ROI within a longitudinally unbounded object can be exactly reconstructed if the ROI is smaller than the region that can be completely covered by the x-ray tube-detector during a scan along the circle-plus-two-arc orbit.

On the other hand, both $h_{|\omega|}(n)$ and $h_{j\omega}(n)$ involved in the reconstruction algorithm further lessen the ROI that can be exactly reconstructed. As shown in (15), the filtering by $h_{|\omega|}(n)$ is implemented latitudinally in obtaining $f_{c_1}(\vec{r})$. Since the object to be reconstructed is latitudinally bounded, $h_\omega(n)$ incurs no contamination to $f_{c_1}(\vec{r})$. However, the filtering by $h_{j\omega}(n)$ is implemented longitudinally in reconstructing $f_{c_2}(\vec{r})$ (20), and incurs contamination to $f_{c_2}(\vec{r})$ because of the longitudinal truncation. Similarly, the filtering by $h_{j\omega}(n)$ incurs contamination to $f_{a_i}(\vec{r})$ (i={1, 2}). Fortunately, both $h_\omega(n)$ and $h_{j\omega}(n)$ are square summable and drop dramatically, and make the contamination depth resulting from them to $f_{c_1}(\vec{r})$, $f_{c_2}(\vec{r})$, $f_{a_1}(\vec{r})$ and $f_{a_2}(\vec{r})$ very limited.

Theoretically, data redundancy can be used to improve the signal to noise ratio (SNR) of a reconstructed image in CBVCT. However, unlike nuclear medicine, acquiring redundant projection data in an x-ray CBVCT may result in unnecessary radiation to a patient. Therefore, a candidate scanning orbit for application in an x-ray CBVCT should keep the data redundancy as low as reasonably achievable (ALARA criterion) while satisfying the data sufficiency condition and maintaining the image quality of a reconstructed image clinically acceptable. The circle-plus-two-arc orbit with the cone beam FBP reconstruction algorithm presented here is one that meets the ALARA criterion. Hence, the evaluation of its performance, such as the quality of the reconstructed image as a function of arc orbit angle sampling interval, arc orbit spanning range, and x-ray source quantum noise levels, as well as its capability to regionally reconstruct a longitudinally unbounded object, is practically important. In order to avoid the transition between the circular data acquisition and the arc data acquisition, the circle-plus-two-arc orbit can be implemented through a "quasi" spiral scan. In that scan, the x-ray tube-detector mounted on a circular gantry continuously rotate. The circular sub-orbit is realized by acquiring 2-D cone beam projections at evenly distributed angular positions along one circle of the x-ray source trajectory while the tilting angle of the gantry is 0° (see FIG. 4B). The arc sub-orbits are realized by acquiring 2-D cone beam projections at both the top and bottom arcs. The quality of the reconstructed images is still acceptable while the arc sub-orbit sampling interval is only half the circular sub-orbit sampling interval. That means that the total turns of the "quasi" spiral scan in the circle-plus-two-arc orbit can be decreased significantly. Hence, the data acquisition time along the arc sub-orbits can be reduced remarkably. Such a significant decrease in data acquisition time is practically important in the application of CBVCT in the image-guided interventional procedures.

Th capability of the cone beam FBP algorithm to regionally reconstruct a longitudinally unbounded object has been verified. The survival of the algorithm from the truncation problem is essential for its application in CBVCT. On the other hand, in the case of shortened arc sub-orbits that violate the data sufficiency condition, a regional exact reconstruction can still be obtained. That means that the spanning range of the arc sub-orbit can be lessened if only an ROI within the object is to be reconstructed.

In implementing the algorithm on a computer system, the reconstruction load is divided into several parts and run in parallel on a RACE parallel computation system which is a scalable multi-processor-based system and is provided by Mercury Computer Systems. Initially, a RACE with 8 upgraded processors will be used, so that the reconstruction time of the algorithm will be 10–12 minutes. Further reducing the reconstruction time by parallel computation to 2 minutes for $512^3$ matrix reconstructions, for 288 projections with 512×512 pixels per projection, can be achieved using a RACE having 16–32 processors with 1024 Mbytes RAM at a relatively low cost.

Figure 7:
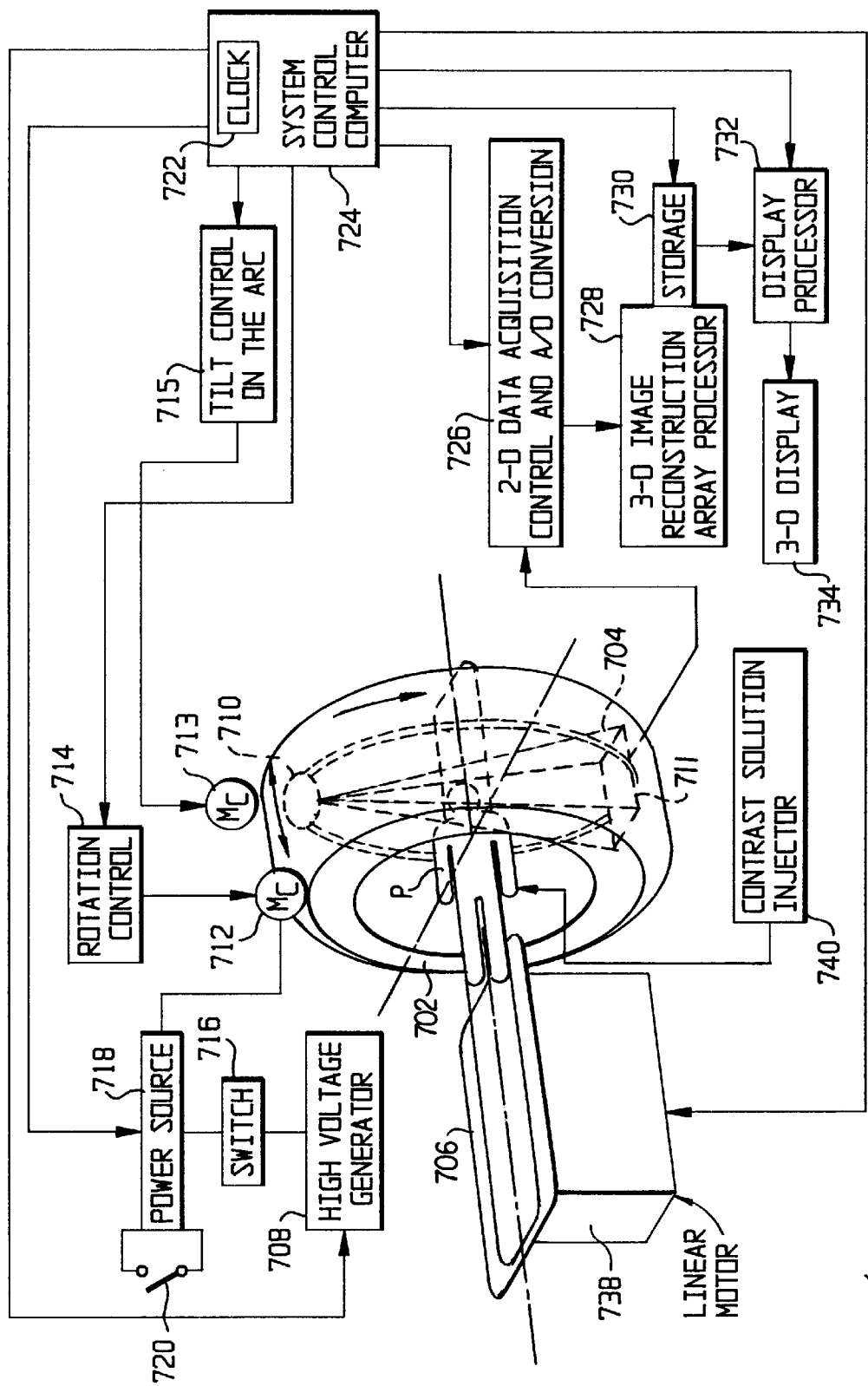
FIG. 7 is a plan diagram of a system on which the preferred embodiment is implemented.

In a standard CT, a 3-D reconstruction is obtained by stacking a series of slices. In an CBVCT, a direct reconstruction of an object can be obtained. Referring now to FIG. 7, it is shown how a CBVCT system 700 of the present invention can be used to obtain a direct 3-D reconstruction of an object. It should be understood that the CBVCT scanning apparatus 700 is illustrated in a simplified block diagram form. The invention may preferably be employed in conjunction with such a CBVCT scanning apparatus to generate a 3-D reconstruction matrix of the object. Based on the 3-D reconstruction matrix, the desired three-dimensional display can be obtained.

A CBV CT scanning apparatus examines a body P using a cone shaped radiation beam 704 which traverses a set of paths across the body. As shown in FIG. 7, an x-ray source 710 and a 2-D detector 711 such as a flat-panel detector are mounted on a gantry frame 702 which rotates around the body P being examined. The operating voltage for the x-ray source is obtained from a conventional high-voltage generator 708 in such a manner that the x-ray source 710 produces the desired cone-shaped beam of radiation when the high-voltage is applied to it. The high-voltage generator 708 is energized by means of a power source 718, through a switch 716.

A first motor 712 is also powered by the power source 718 such that it drives the gantry frame 702 in its orbit about the body, for example, in a clockwise direction as shown by the arrows adjacent to the frame. The power source 718 is turned on by means of switch 720 or other conventional control devices, in order to initiate a measurement sequence. A speed control circuit 714 is used to control the speed of rotation of the gantry frame 702 and to provide an output control signal which indicates when the speed of the motor 712 is at the desired level for taking measurements. The output from the rotational control 714 may also be utilized to operate the switch 716 such that the high-voltage generator 708 is only turned on when the gantry frame 702 is driven at the desired speed for making measurements.

In order to obtain the arc measurements as previously discussed, a tilt control 715 is utilized to cause the gantry frame 702 to tilt by a relatively small angle of ±15° to ±30°, by means of the gantry frame tilt motor 713. That tilting allows the acquisition of arc projection data on the perpendicular arc. Such geometry results in a complete set of data for an object with a 25–40 cm diameter corresponding to a 37–60 cm field at the detector 711 with a magnification of 1.5. Although the tilting of the gantry 702 is generally available in a standard CT gantry, to acquire arc projections, the minimal modification of a standard CT gantry has to be made such that the tilting of the gantry, the x-ray exposure timing and the projection acquisition are synchronized by a system control computer 724 having a clock 722.

The gantry can be based on modifications of existing equipment made by such companies as GE, Siemens, Toshiba and Marconi. Such modifications include replacing the one-dimensional detector with an II-CCD detector or a silicon or selenium thin film transistor array FPD and the old computer system and its control interface boards with a new host computer and new interface boards. As explained in the co-pending applications cited above, a slip ring is preferably used to permit communication between equipment on the gantry and equipment off the gantry. Initially, volume scanning speed will be only limited by the maximum frame rate of the real time FPD. Currently available real time FPDs have a frame rate of 15–120 frames/sec. The flat panel researchers predict that the future frame rate can be up to 120 frames/sec. (1K×1K pixels/frame) and 480 frarnes/sec with reduced vertical readout lines (256×1K pixels/frame). When the frame rate of the detector is increased to 480 frames/sec. for a large size FPD in the future, the volume scanning time of entire lungs will shorten to 1–2 seconds depending on the required resolution and/or the projection number can be increased to improve image quality. Compared to II-based VTDA systems, the FPD-based CBVCT system represents a significant technologic advancement due to using flat plane detector, slip ring technology, and cone beam reconstruction algorithms that result in accurate reconstruction. In addition, the CBVCT system can incorporate a scaleable multiprocessor-based parallel computing system (8–32 processors) provided by Mercury Computer systems.

Figure 4B:
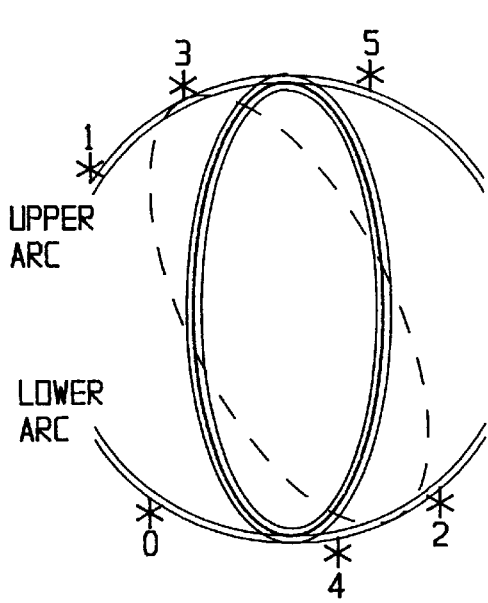
FIG. 4B is a diagram of a quasi-spiral scan used to implement the circle-plus-two-arc orbit.
Figure 10:
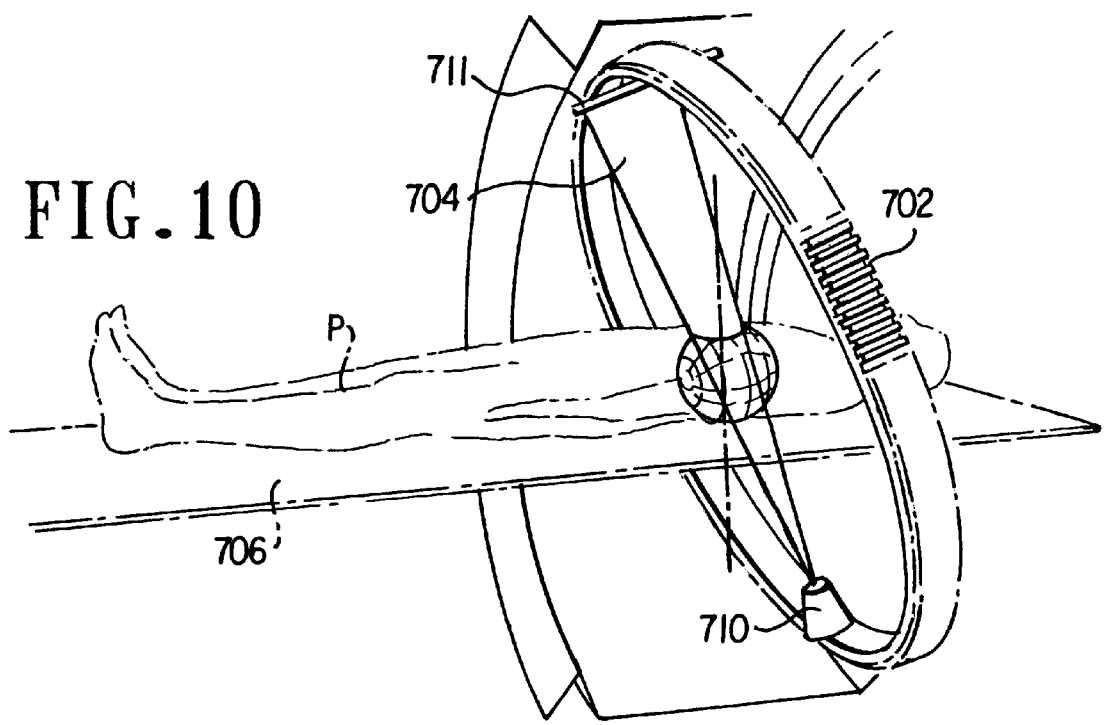
Figure 11:
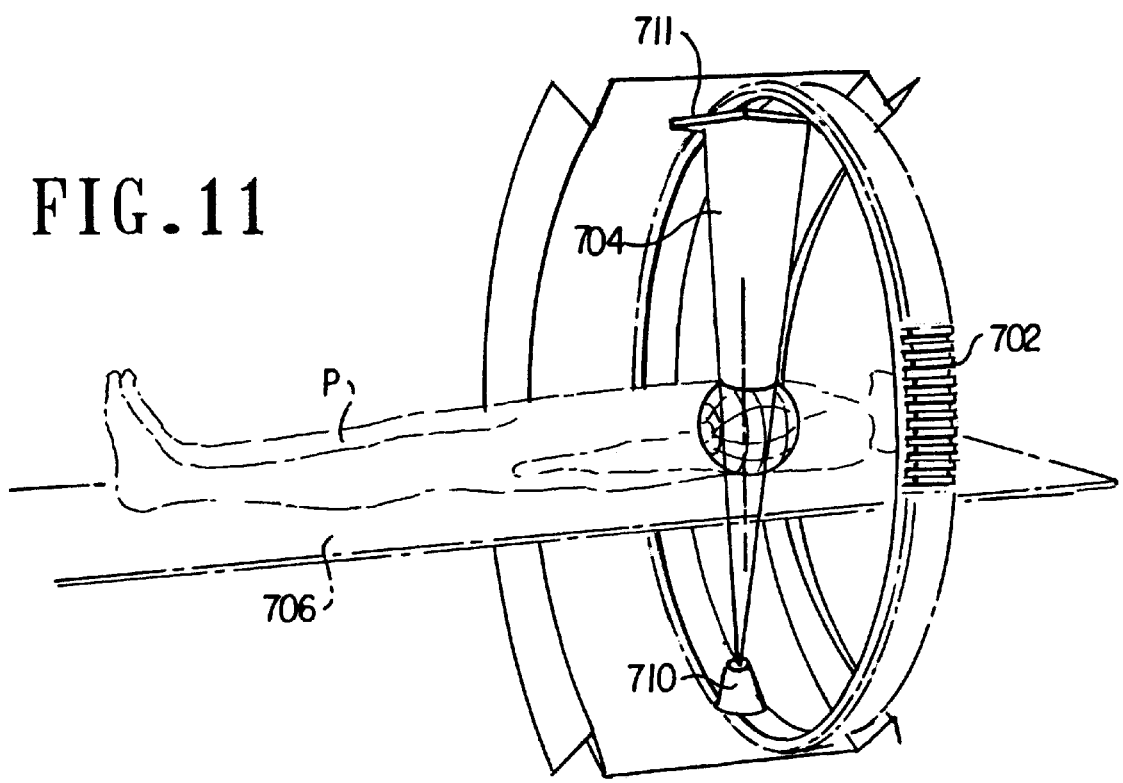

A specific scanning protocol will now be described which implements −15° to +15° tilting to obtain 25 cm coverage in the z direction. This protocol consists of four steps: 1) Positioning gantry—Before starting the scan, the gantry tilts to −15° to prepare for CPA scan; 2) Arc-Projection Acquisition (Gantry tilt-in)—While the gantry is tilting from −15° to 0°, the x-ray tube and detector rotate, taking projections only at 0° (on the upper arc) and 180° (on the lower arc) of the rotation angle positions to obtain two arc projections per rotation; 3) Circle Projection Acquisition—When the gantry tilts to a 0° tilting angle, the gantry stops tilting, and the x-ray tube and detector rotate to acquire multiple circle projections; and 4) Arc-Projection Acquisition (Optional Gantry tilt-out)—. If necessary, after completing circle scan, the gantry tilts from 0° to +15°, while the x-ray tube-detector rotates, taking arc projections as in step 3. FIG. 4B shows a circle-plus-arc scan with six arc projections taken at the positions labeled 1 through 6 along the upper and lower arcs. FIG. 10 shows exposure with the gantry tilted, while FIG. 11 shows exposure with the gantry not tilted.

To reduce circle-plus-arcs CBVCT scan time, the quasi-spiral scan mode of the gantry is used because during the scan, the x-ray tube and detector continue rotating on the gantry while the gantry is tilting and the gantry stops tilting at 0° tilting angle to acquire circle projections. The quasi-spiral scan mode eliminates the need to stop the rotation of the x-ray tube and the detector during the scan and reduces the transition time between arc acquisition and circle acquisition. In addition, a complete set of cone beam projection data can be achieved using two opposite half arcs (1–4 arc projections) and a single circle scan orbit. For example, as shown in FIG. 4B, arc projections can be taken only at locations 1–4, or only at locations 5 and 6, corresponding to gantry tilt-in without tilt-out. With two complete arcs, e.g., projections at all of locations 1–6 of FIG. 4B, image quality is better. Therefore, gantry tilt-out is an optional mode which can be eliminated in the interest of time constraints. In other words, if the imaging task requires high temporal resolution to reduce motion artifacts or to obtain dynamic information, only a gantry-tilt-in arc scan and a circle scan are required, which reduce the arc scanning time to half.

In detection of lung cancer, since only 25 cm of the trunk of the body will be viewed per scan in the z direction, the gantry needs to be tilted ±15° at most. The volume scan time should be 4–8 seconds, depending on the achievable tilt speed, how large the segment in the z direction is actually viewed and the acquisition rate of the detector. The system provides computer-controlled gantry tilt and synchronized x-ray exposures with 2 exposures/sec for arc projection acquisition. A bidirectional encoder, which is used on the current gantry to track projection angle in the step mode, will be installed to track the projection angle on the arc. The tilt speed on the arc will be 7.5°/sec and the projection numbers on the arc will be 4 to 12.

Since the CBVCT system is based on an existing helical CT gantry and table, the system should have an existing computer-controlled table movement capability. With little modification, a circle-plus-line (CPL) scan can be achieved. Two bidirectional encoders are added: one is to track the longitudinal position of the x-ray source and the detector, and another to track the angular position of the source and detector. Then the system will be modified to synchronize x-ray exposure with 2 pulses/sec for line projection acquisition. Since only 25 cm of the trunk of the body in the z direction will be viewed per scan, the patient table is fed for 25 cm with the maximum feeding speed of 12.5 cm/sec., and then the volume scan time should be within 4–8 seconds, depending on the achievable feeding speed, required resolution and the actual size of the coverage in the z direction per scan. For detection of cancers such as lung cancer, circle-plus-lines and helical cone-beam scanning can also work.

In addition to the method above to acquire circle and arc projections, alternatively, the circle-plus-arc geometry can be implemented in one of the following two ways. In the first and preferred of the three methods, the gantry 702 is tilted to a small angle (±15° to ±30°.) and then the x-ray tube 710 and the 2-D detector 711 are rotated while the gantry 702 is tilted. A half set of arc projections will be acquired only when the x-ray tube 710 and the 2-D detector 711 are at the rotation angles of 0° and 180°. When the tilted angle becomes zero, the circle projections will be acquired at the preset rotation angle positions. When the circle projection acquisition is completed, the gantry 702 will be tilted toward −15° to −30°. Another half set of arc projections will be acquired only when the x-ray tube 710 and the 2-D detector 711 are at the rotation angle of 0° and 180°.

The second alternative method is to mechanically modify a standard CT gantry such that two short arc orbits are added to the gantry, and the x-ray tube 710 and the 2-D detector 711 can be moved on the arc to acquire the arc projections and on the circle to acquire the circle projections. One arc constitutes the orbit of the x-ray tube 710 and the other arc is the orbit of the 2-D detector 711. The two arc orbits are mounted 180° apart from each other. The x-ray tube 710 and the 2-D detector 711 are synchronously moved on the arc orbits to acquire arc projections. Then, the x-ray tube 710 and the 2-D detector 711 are rotated on the gantry to acquire circle projections.

Mounted on the gantry frame 702 opposite the x-ray source 710 is a 2-D detector 711 which has a dynamic range equal to or greater than 1000:1 and an image lag of less than 10%, for example a selenium thin film transistor (STFT) array or a silicon STFT array, in order to provide 2-D projections that correspond to an x-ray attenuation signal pattern. The x-ray source 710 and the 2-D detector 711 are mounted on the gantry frame 702 in such a manner that they both move synchronously.

The cone-shaped beam of radiation 704 generated by the x-ray source 710 is projected through the body or object under test. The 2-D detector cone measures the radiation transmitted along the set of beam paths across the cone.

Alternatively, a continuous series of two-dimensional detectors (not shown) can be fixedly mounted proximate to the gantry frame 702 and the x-ray source 710 is mounted to the gantry frame such that, upon rotation of the gantry frame, the cone-shaped radiation beam 704 is projected through the body P under test and sequentially received by each of the series of detectors.

A 2-D projection acquisition control and A/D conversion unit 726, under control of the scanning pulses sequentially obtained from the system control computer 724, which includes the clock 722, receives a sequence of outputs corresponding to different lines of the 2-D detector 711. Each line of the 2-D detector consists of many detection cells (at least 100). The output of each detector cell represents a line integral of attenuation values measurable along one of the respective beam paths. The cone-shaped beam 704 subtends a cone angle sufficient to include the entire region of interest of the body. Thus, a complete scan of the object can be made by merely orbiting the gantry frame 702 supporting the x-ray source 710 and the 2-D detector 711 around the body to acquire the 2-D projection signals at different angular positions.

The analog-to-digital conversion unit 726 serves to digitize the projection signals and to save them in the 3-D image reconstruction array processor 728 and storage device 730. The method employed by the 3-D image reconstruction array processor 728 is the invented algorithm described herein. The 3-D image reconstruction array processor 728 serves to transform the digitized projection signals into x-ray attenuation data vectors. The x-ray attenuation data matrix corresponds to x-ray attenuation at spaced grid locations within the body trunk being examined. Each data element of the matrix represents an x-ray attenuation value and the location of the element corresponds to a respective 3-D grid location within the body.

In accordance with the principles of the invention discussed previously, a display processor 732 obtains the data stored as 3-D x-ray attenuation signal patterns in the memory storage 730, processes the data as described above, and then the desired 3-D images are displayed on a 3-D display device 734.

The 3-D image reconstruction array processor 732 may, for example, be comprised of an ULTRA SPARC-10 model workstation, available from Sun Microsystems, Inc. of Mountain View, Calif. 94043. Another system is the Mercury Computer Systems RACE Platform, which is a multiprocessor-based parallel computing system scalable up to a few hundred processors. The reconstruction algorithm presented above is well suited to such parallel processing devices, since the various terms in the reconstruction can be calculated separately and summed. The use of a Storage Concept real-time storage system allows the acquisition of up to 64 GB of data continuously in real time.

The patient P is placed on a patient table 706 which is made to slide by a linear motor 738 or some such device under control of the system control computer 724. Alternatively, the patient P can be placed on a fixed table, and a gantry frame holding the detector and the source can be moved over the patient P.

An optional contrast solution injector 740, known in the art, can be used to inject a contrast solution for improved imaging. However, the invention can be used without such an injector.

Figure 8:
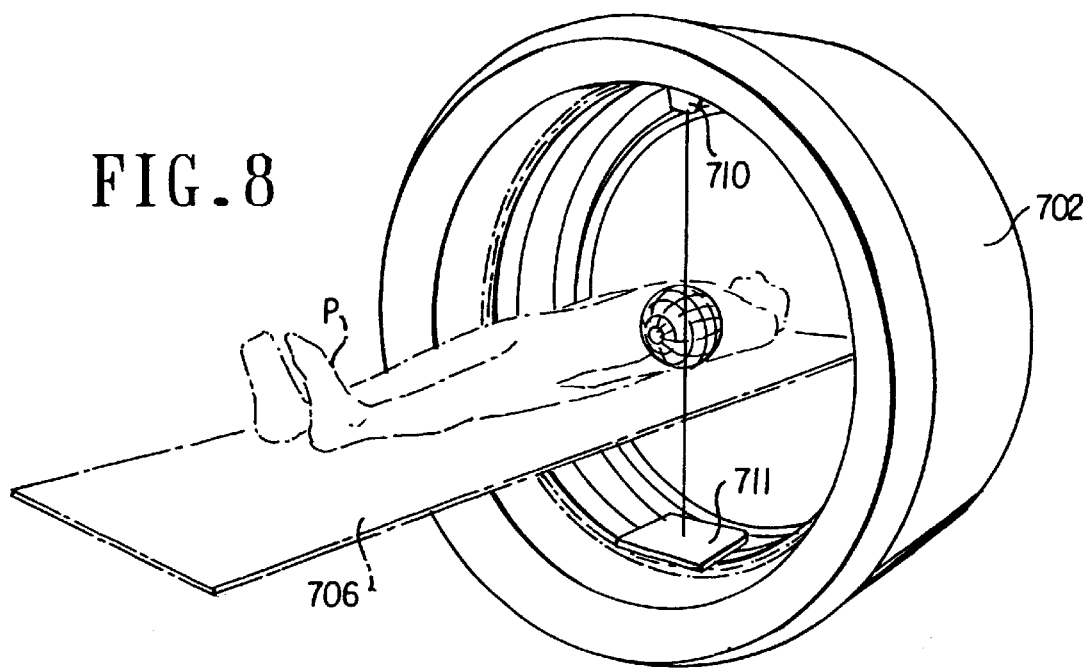
FIGS. 8–11 show stages in the operation of the system of FIG. 7.
Figure 9:
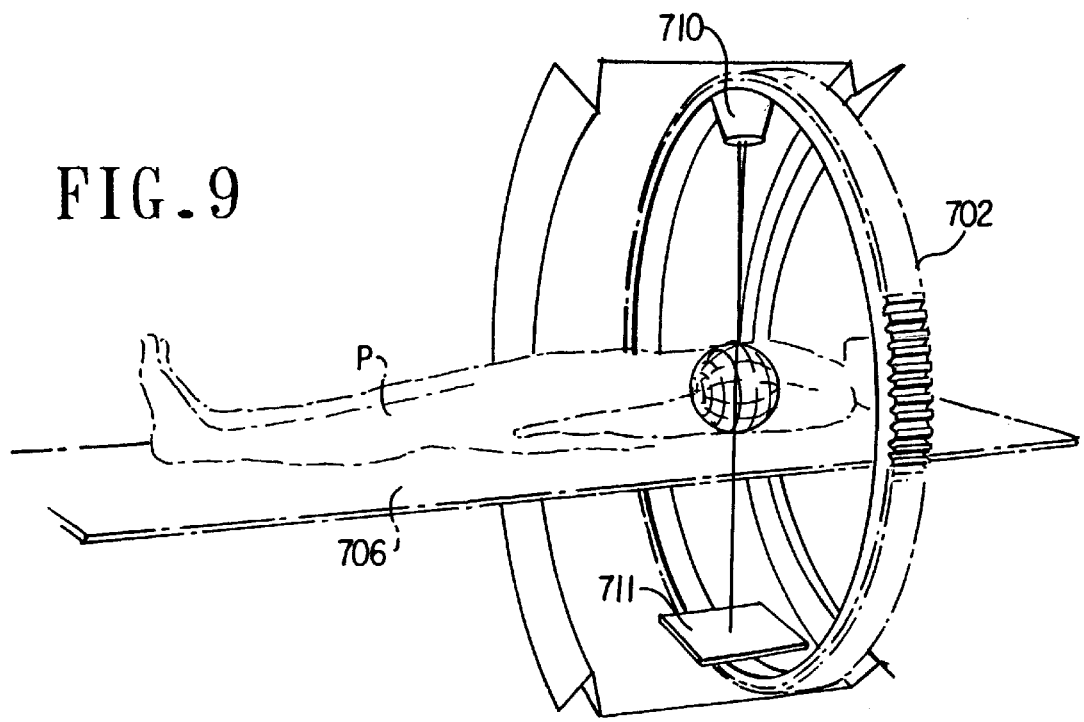

An example of the operation of the CBVCT tomography system 700 will now be explained with reference to FIGS. 8–11. As shown in FIGS. 8 and 9, the patient table 706 bearing the patient P is moved into the gantry 702 so that the region of interest ROI lies between the source 710 and the detector 711. As shown in FIG. 10, to take the arc projections, the gantry 702 is tilted, and a cone beam 704 is emitted when the angular orientation of the source 710 is at 0° and 180° from a predetermined base location. As shown in FIG. 11, to take the circle projections, the gantry is righted, and the source 710 emits the cone beam 704 repeatedly as the gantry rotates.

To decrease the total acquisition time, the sampling rate on the arcs can be reduced relative to the sampling rate on the circle. In addition, or as an alternative, the arc projections can be taken by using only a tilt-in of the gantry 702. A tilt-out of the gantry can be used to take additional arc projections to improve image quality.

Developing and optimizing an x-ray scatter control and reduction technique is one big challenge for CBVCT because CBVCT is less immune to scatter than fan-beam CT. CBVCT image contrast is reduced by scatter without an effective control technique. Scatter can be countered with a hybrid technique that uses an air gap technique and an antiscatter grid to control scatter and a practical software correction technique for detected scatter. One of the major differences between fan beam slice CT and CBVCT is x-ray beam collimation. Using very narrow slit collimation in fan beam CT reduces scatter-to-primary ratio (SPR) to 0.2 or less. On the other hand, using a large cone collimation in cone beam geometry with only an air gap technique results in an average SPR up to 1.

To overcome that limitation, a software correction technique is used to correct for detected scatter and to reduce overall average SPR to 0.2 or less. Convolution filtering techniques and scatter detected by the FPD are used to estimate scatter distribution and then subtract it from the total projection. A known convolution filtering technique taught in Love, L. A., and Kruger, R. A., "Scatter estimation for a digital radiographic system using convolution filter," *Med. Phys.* 1987; 14(2):178–185, was implemented for an image intensifier (II)-based imaging system and produced an average percentage error of 6.6% for different anatomy and different clinical applications. That is equivalent to a reduction of SPR by a factor of up to 14. Even better scatter correction results can be achieved for an FPD-based system because there is no veiling glare component, compared to an II-based system where that is a more dominant component. Based on previous studies and preliminary results, it is anticipated that the average SPR in each cone beam projection can be reduced to 0.2. That is the equivalent SPR achievable in a fan beam slice CT, using a hybrid scatter correction technique (software correction plus air gap). That analysis and the preliminary results show that with the above-noted x-ray scatter reduction and correction techniques, the FPD-based CBVCTM system provides more than adequate low contrast resolution.

The preferred embodiment combines an air gap technique with an antiscatter grid and a software correction technique for residual scatter. A 10–15 cm air gap technique is an effective method to prevent large angle scatter radiation from reaching the detector and to reduce average SPR to less than 2. It is contemplated that in the CBVCT system, the distance from the rotation center to the detector will be about 40 cm. With that geometry, the air gap is more than 15 cm to achieve an average SPR less than 2.

One example of an efficient x-ray scatter rejection grid includes a focused, tantalum, air-interspaced grid with a 10:1 grid ratio and 80 lines/inch. The grid strips are suspended between a pair of carbon fiber plates and aligned parallel to the axis of rotation. A scatter-to-primary ratio (SPR) of approximately 1.0 can be achieved with 100° kVp and a moderate increase of the exposure level to keep the noise level unchanged. With a stationary grid there are grid artifacts. To avoid such grid artifacts, the grid can be reciprocated with a computer-controllable speed to blur the grid strip artifacts.

The residual scatter present within the projection images is removed based on a convolution-filtering method to estimate residual scatter distribution in each projection image. In the convolution filtering method, residual scatter is modeled as a low pass, spatially filtered version of the total projection (scatter plus primary). After estimating residual scatter in each projection, the residual scatter radiation is then subtracted to obtain primary distribution for reconstruction. That technique effectively reduces SPR from 1.0 to 0.2 or less.

Figure 12B:
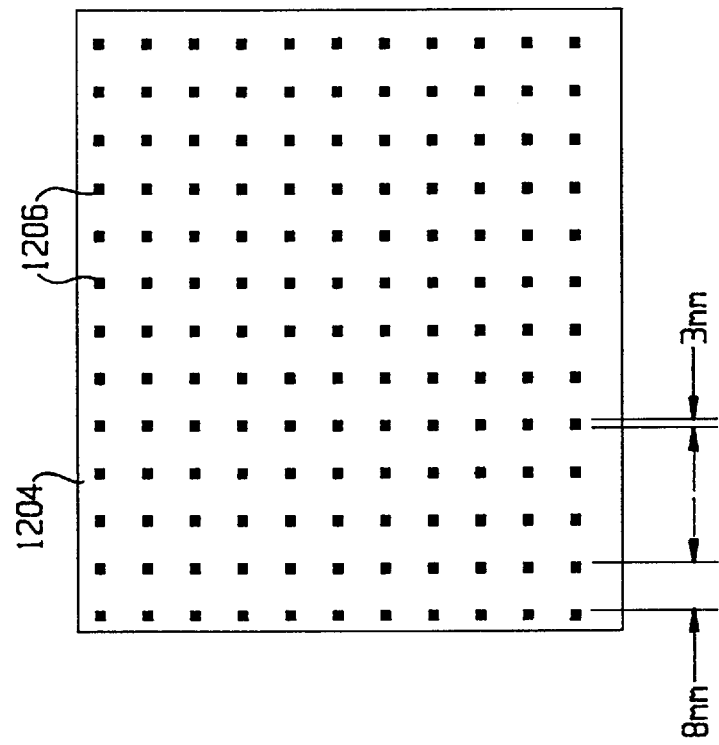
FIGS. 12A and 12B show a setup for taking scout images for scatter correction.
Figure 12A:
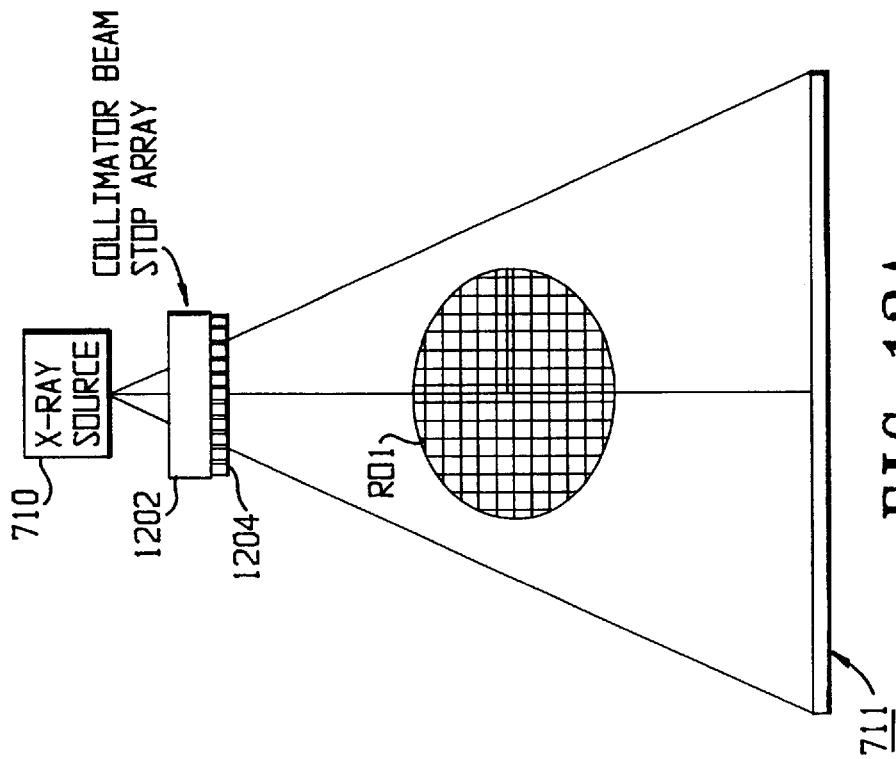

The conventional convolution filtering method requires two x-ray projections at each projection angle to accurately estimate residual scatter: one with a beam stop array for calculating two scaling factors and another without the beam stop array. That is not practical and would significantly increase patient dose in CBVCT. To overcome those difficulties, the preferred embodiment uses scout images for estimating scatter distribution in "real time" for each patient. Before starting to scan, one scout projection image is acquired, as in a standard fan beam CT. Traditionally, the scout images are used for positioning, and surveying body size to adjust the x-ray exposure levels in real time and reduce patient dose Before acquiring scout images, as shown in FIGS. 12A and 12B, a square matrix 1204 of small lead ball bearings 1206 is placed between the x-ray collimator 1202 and the region of interest ROI. Both primary and sampled scatter distributions are estimated from the scout images with the lead beam stop array. The estimated primary images are used for a scouting purpose. The scaling factors for estimating scatter distribution and the convolution kernels at sampled angle positions can be determined. Then the scatter distributions are estimated using the convolution kernel at corresponding angle positions and subtracted from the detected projections. To reduce radiation dose to the patient and computation load, only a minimum number of required scout images are acquired. Only a few scout images are needed because the accuracy of the method is not highly dependent on the exact shape of the convolution kernel, so long as its dimensions are large enough. The exponential kernel is used for the estimation of residual scatter because a 2D exponential kernel is an optimum formation.

Another technique which can be used in the present invention to improve imaging is the ultra-high-resolution volume-of-interest (VOI) reconstruction mode. That technique can be used to focus on a suspicious lesion.

It is known in the art for flat panel detectors to have zoom modes. One source of such flat panel detector is Varian Imaging Products of Mountain View, Calif., U.S.A. The Varian PaxScan 2520 flat panel detector has the following characteristics: size=19.5×24.4 cm, frame rate=15–120 frames per second, image lag <10%, pixel pitch=127 $\mu$m, A/D=16 bits, exposure range=1–3000 uR, DQE=65%, dynamic range=2000–30,000:1. Even larger flat-panel detectors are known in the art, e.g., 50 cm×50 cm.

The zoom mode of a flat panel detector such as a Varian flat panel detector is used to acquire projection data for ultra-high VOI reconstruction. In the zoom mode, the detector can acquire a random block of 768×960 pixels at 30 frames/sec. with the full 4 lp/mm resolution of the sensor. The pixel size of the detector, as noted above, is 127 $\mu$m. A dual-focus spot x-ray tube is used, having focus spots of 0.3 and 0.6 mm. Ultra-high-resolution VOI can use a 0.3 mm focus spot, so that the focus spot size will not be a limiting factor of the spatial resolution for the VOI mode. Therefore, the FOV (field of view) of the zoom mode is 9.75×12.2 cm. To reduce unnecessary radiation to the patient, a collimator limits the radiation to within the ROI (region of interest) in the VOI acquisition. A narrow strip of collimation (~2cm wide) is needed. If the ROI is larger than 12.2 cm in diameter, the projection data acquired in ultra-high VOI mode are truncated in the lateral direction. There are some streak artifacts if the reconstruction is obtained from the truncated data without preprocessing the data. The conventional method to deal with truncated projection data is to tail the projection data with a cosine wave before filtering (Z. H. Cho, E. X. Wu, S. K. Hilal: "Weighted backprojection approach to cone-beam 3D projection reconstruction for truncated spherical detection geometry," *IEEE Trans Med Imaging* 13(1), 110–122, March, 1994). Fortunately, in the present case, the complete information in the region out of VOI is already available from the previous lower resolution scan. That information can be used to tail the truncated projection data and then complete the VOI reconstruction. Computer simulation indicates that such an algorithm eliminates the reconstruction artifacts introduced by truncated data within VOI. Such a technique is anticipated to be better than the conventional method. It is fuirther anticipated that the ultra-high-resolution VOI reconstruction technique can provide up to 5.0 lp/mm resolution with a justifiable increase of the x-ray dose. The above-disclosed VOI technique can be used to detect cancers, such as breast and lung cancer.

A FPD-based CBVCT system will provide better contrast and spatial resolution and better geometric accuracy than an II-based CBVCT system. Recently, a new technology of large area flat panel solid state detector array has been developed by several groups. A high resolution, high frame rate, amorphous silicon (a-Si:H) FPD using a phosphor screen and a photodiode array to convert incident x-rays to a charge image has been developed. Also, a selenium FPD has been developed by other groups using a uniform layer of an x-ray sensitive photoconductor, selenium, for a direct conversion of x-rays to an electronic image. In addition, a real time FPD for fluoroscopic images has been developed. In spite of their differences, these image sensors have some common potential advantages over other detectors: compactness, high DQE, absence of geometric distortion and veiling glare with the benefits of high resolution, high frame rate, high dynamic range, small image lag (<1%) and excellent linearity (~1%). The FPD has almost the same DQE as an II within the diagnostic radiation range. These advantages of the new FPD over an II-CCD detector make it a good candidate for the detector used in CBVCT. Therefore, a FPD-based CBVCT system will make CBVCT a superior technique. In the past two years, the development of the TFT detector has been exciting and progressed from the research phase to the production phase. Six companies have started to manufacture this type of detector.

The FPD-based CBVCT angiography system has better spatial resolution and low contrast resolution than II-based systems. The FPD-based system has better spatial resolution than a helical CT and near equal low contrast detectability in comparison to a helical CT.

Two alternatives to the circle-plus-multiple-arcs orbit can be used to obtain data sufficient for exact reconstruction.

Figure 4C:
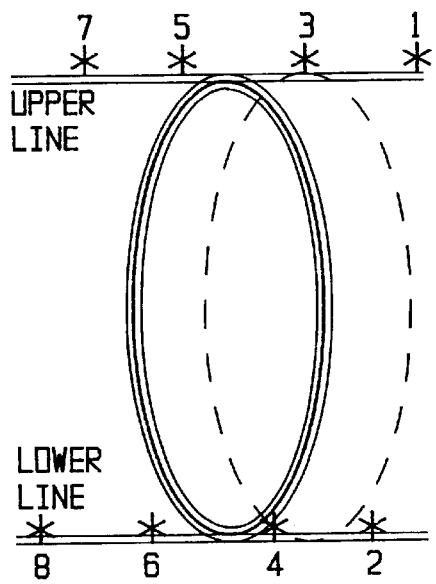
FIG. 4C is a diagram of a scan used to implement a circle-plus-two-line orbit.

FIG. 4C shows an orbit for taking a scan over a circle plus multiple (in this case, two) lines. That orbit allows at least 25 cm coverage in the Z direction. Before starting the scan, the patient on the table is positioned to −12.5 cm from the center of the scanner to prepare for circle-plus-line (CPL) scan. While the table is moving toward the center of the scanner, the x-ray tube-detector rotates, taking projections only at 0° (on the upper line) and 180° (on the lower line) of the rotation angle positions to obtain two line projections per rotation. When the table is at the center of the scanner, the table stops moving, and the x-ray tube and detector rotate to acquire multiple circle projections. After acquisition of the circle projections, the table moves toward the position of +12.5 cm from the center of the scanner, while the x-ray tube and detector are rotating, taking more line projections as above. The reconstruction algorithms are those taught by Hu.

To reduce CPL scan time, the "quasi" spiral scan mode of the gantry is used because during the scan, the x-ray tube and detector continue rotating on the gantry while the table is moving and the table stops at the center of the scanner to acquire circle projections. This scan mode will eliminate x-ray tube-detector rotation-stops during scan and reduce the transition time between line acquisition and circle acquisition. It can also be noted that we actually acquire line projections along two lines: the upper and lower lines, as shown in FIG. 4C which shows the implementation of CPL orbit using "quasi" spiral scan on a spiral gantry with 8 line projections at the positions numbered 1 through 8. This is because this can reduce the sampling rate on a single line and increase line-scanning speed when using "quasi" spiral mode.

Figure 4D:
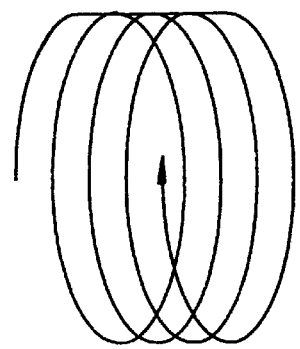
FIG. 4D is a diagram of a scan used to implement a helical orbit.

A spiral scan will now be explained with reference to FIG. 4D. While the table is moving through the gantry, the x-ray tube and detector rotate, taking projections at multiple angle positions to obtain multiple spiral cone beam projections per rotation. Depending on the achievable frame rate of the detector, the spiral scanning time will be 2–8 seconds and the total spiral rotation angle will be from 180° plus cone angle to 720° to cover 6.5 cm to 25 cm in the z-direction. The reconstruction algorithms are those taught by Wang, G. E., Lin, T. H., Chen, P. C., and Shinozaki, D. M., "A General Cone-Beam Reconstruction Algorithm," *IEEE Transactions on Medical Imaging*, Vol. 12(3):486–496 (1993), and in Wang, G. E., Lin, T. H., and Chen, P. C., "Half-Scan Cone-Beam X-Ray Microtomography Formula," *Scanning*, Vol. 16, pp. 216–220 (1994).

Based on currently available FPDs, a spiral scan should have a scanning speed of 2–8 seconds, a z-coverage of 65–250 mm and a slice thickness in the z direction of 0.17–0.67 mm. That scan offers the advantages of more uniform sampling and ease of implementation. The circle-plus-arcs and circle-plus-lines scans should both have a scanning speed of 4–8 seconds, a z-coverage of 130–250 mm and the same slice thickness as that for the spiral scan. The circle-plus-lines orbit is currently the best to address truncation. The circle-plus-arcs orbit has the advantage that it requires no patient transition during the scan; that is, the patient remains still.

The scanning times listed above are estimated based on the frame rate of currently available FPDs (60–120 frames/s) and the spiral gantry speed for a used spiral CT gantry (1 s/revolution). Existing FPDs are specially designed for radiographic or fluoroscopic imaging not for fast tomographic imaging. Once a large size FPD-based CBVCT becomes feasible, a large size FPD specially designed for fast tomographic imaging with high speed and low image lag will be developed. If the frame rate of the detector is increased to 960 frames/sec. for a 25 cm×50 cm FPD, the spiral scan time for 33 cm coverage will be 1–2 seconds depending on gantry speed and table moving speed.

To deal with the projection truncation problem, the following three measures can be taken. First, when determining which orbit and related algorithm will be used for reconstruction, the one with the smallest contaminated depth should be used. Second, when measuring the total dose to a patient, the dose received in the contaminated region due to projection truncation should be included. Third, when acquiring projection data using the CPL or CPA, the detector in the longitudinal direction should be slightly larger than the ROI.

If it is necessary for the ultra-fast readout of FPD, a subtraction algorithm can be used to reduce the effect of image lag. In such an algorithm, the previous N weighted projections will be subtracted from the current projection. The weighting factor for each previous projection will be determined by the lag measured vs. frame numbers subsequent to the frame in which it was generated. Then the final image will be reconstructed from image lag-corrected projections.

While a preferred embodiment of the present invention has been set forth above, those skilled in the art will recognize that other embodiments can be realized within the scope of the invention. For example, numerical values and the names of specific products are illustrative rather than limiting. Also, to achieve the circle-plus-two-arcs or circle-plus-multiple-arcs orbit, any suitable equipment and mode of operating it can be used. Furthermore, the particular algorithms presented herein are illustrative rather than limiting. Moreover, while the utility of the invention has been presented with particular attention to lung cancer, it can be used for other malignancies. Therefore, the invention should be construed as limited only by the appended claims.

APPENDIX

A. Derivation of the Reconstruction Algorithm for Arc CB Projections $(x_o, y_o, z_o)$ is the fixed coordinate system, and $(X_L, Y_L, Z_L)$ is the local coordinate system rotating rigidly in phase with the virtual detector plane. The arc orbits are within the plane determined by $(x_o, y_o)$. In the local coordinate system $(x_L, y_L, z_L)$, Grangeat's formula can be written as:

$$\frac{|OS|^2}{|\overrightarrow{OS} \times \vec{n}|^2} \frac{\partial}{\partial l} \int_{-Z_i}^{Z_i} \int_{-Y_i}^{Y_i} \frac{|\overrightarrow{SO}|}{|\overrightarrow{SA}|} P_\beta(Y,Z)\delta(Y\sin\Theta + Z\cos\Theta - l)dYdZ = \quad (A\text{-}1)$$

$$\frac{\partial}{\partial \rho} Rf(\overrightarrow{OS}\cdot\vec{n},\vec{n})$$

where $Rf(\overrightarrow{OS}\cdot\vec{n},\vec{n})$ is the Radon transform over the shadowed plane with norm vector $\vec{n}$ which passes through the source focal point S, $Y_i$ and $Z_i$ are the integral limits along the Y and Z axes respectively, and $P_\beta(Y,Z)$ is the cone beam projection at angle $\beta$ along the arc orbits.

In the local coordinate system $(x_L, y_L, z_L)$, $$\overrightarrow{OS}=(D,0,0) \quad (A\text{-}2)$$

$$\vec{n}=(\sin\theta\cos(\phi-\beta),\sin\theta\sin((\phi-\beta),\cos\theta) \quad (A\text{-}3)$$

$$\rho=\overrightarrow{OS}\cdot\vec{n}=D\sin\theta\cos((\phi-\beta)) \quad (A\text{-}4)$$

$$|\overrightarrow{OS}\vec{n}|^2=D^2-D^2\sin^2\theta\cos^2(\phi-\beta)=D^2-\rho^2 \quad (A\text{-}5)$$

$$\overrightarrow{OS}\cdot\vec{n}=\vec{r}\cdot\vec{n} \quad (A\text{-}6)$$

For derivation convenience, by letting $$I(\beta, l, \Theta) \equiv \int_{-Z_i}^{Z_i} \int_{Y_i}^{Y_i} \frac{|\overrightarrow{SO}|}{|\overrightarrow{SA}|} P_\beta(Y,Z)\delta(Y\sin\Theta + Z\cos\Theta - l)dYdZ \quad (A\text{-}7)$$

(A-1) is converted into $$\frac{D^2}{D^2-\rho^2}\frac{\partial}{\partial l}I(\beta,l,\Theta) = \frac{\partial}{\partial \rho}Rf(\vec{r}\cdot\vec{n},\vec{n}) \quad (A\text{-}8)$$

Taking the 1$^{st}$ derivative on both sides of (A-8) and using (A-15) (see below) gives $$\frac{D^2}{D^2-\rho^2}\left[\frac{2\rho}{D^2-\rho^2}\frac{\partial}{\partial l} + \frac{D^3}{(D^2-\rho^2)^{\frac{3}{2}}}\right]I_i(\beta,l,\Theta) = \frac{\partial^2}{\partial \rho^2}Rf(\vec{r}\cdot\vec{n},\vec{n}) \quad (A\text{-}9)$$

In the local coordinate system $(x_L,Y_L,Z_L)$, the Radon plane $SD_1D_2$ can be represented by the equation:

$$lx_L+D\cos\Theta y_L+D\sin\Theta z_L-Dl=0 \quad (A\text{-}10)$$

On the other hand, in the fixed original coordinate $(x_o,y_o,z_o)$, another equation to describe the same Radon plane can be written as $$x_o\sin\theta\cos\phi+y_o\sin\theta\cos\phi+z_o\cos\phi\theta-\rho=0 \quad (A\text{-}11)$$

Through the relation between the local and the fixed coordinate system $$\begin{pmatrix} x_L \\ y_L \\ z_L \end{pmatrix} = \begin{pmatrix} \cos\beta & \sin\beta & 0 \\ -\sin\beta & \cos\beta & 0 \\ 0 & 0 & 1 \end{pmatrix}\begin{pmatrix} x_O \\ y_O \\ z_O \end{pmatrix} \quad (A\text{-}12)$$

and solving (A-10) and (A-11) simultaneously, we have:

$$\sin\theta\cos\varphi = \frac{-D\cos\Theta\sin\beta+l\cos\beta}{(D^2+l^2)^{\frac{1}{2}}} \quad (A\text{-}13)$$

$$\sin\theta\sin\varphi = \frac{D\cos\Theta\cos\beta+l\sin\beta}{(D^2+l^2)^{\frac{1}{2}}} \quad (A\text{-}14)$$

$$\rho = \frac{Dl}{(D^2+l^2)^{\frac{1}{2}}} \quad (A\text{-}15)$$

$$\cos\theta = \frac{D\sin\Theta}{(D^2+l^2)^{\frac{1}{2}}} \quad (A\text{-}16)$$

Consequently, from (A-13) and (A-14), we have $$\tan\varphi = \frac{D\cos\Theta\cos\beta+l\sin\beta}{-D\cos\Theta\sin\beta+l\cos\beta} \quad (A\text{-}17)$$

Considering the variable change from $(\theta,\phi)\rightarrow(\Theta,\beta)$, we get $$\sin\theta d\theta d\varphi = -\frac{D\cos\Theta d\Theta}{(D^2+l^2)^{\frac{1}{2}}}d\beta \quad (A\text{-}18)$$

Further, by introducing (A-15) into (A-9), we get $$\frac{(D^2+l^2)^{\frac{3}{2}}}{D^3}\left[\frac{2l}{D^2}\frac{\partial}{\partial l} + \frac{D^2+l^2}{D^2}\frac{\partial^2}{\partial l^2}\right]I_i(\beta,l,\Theta) = \frac{\partial}{\partial \rho}Rf(\vec{r}\cdot\vec{n},\vec{n}) \quad (A\text{-}19)$$

According to the 3D Radon inverse transform (27), eventually, we have $$f_{a_i}(\vec{r}) = -\frac{1}{4\pi^2}\int\int_{\Omega_i}\frac{\partial^2}{\partial \rho^2}Rf(\vec{r}\cdot\vec{n})d\vec{n} \quad (A\text{-}20)$$

$$= -\frac{1}{4\pi^2}\int_0^\pi\int_{-\frac{\pi}{2}}^{\frac{\pi}{2}}\frac{\partial^2}{\partial \rho^2}Rf(\vec{r}\cdot\vec{n})\sin\theta d\theta d\varphi$$

$$= -\frac{1}{4\pi^2}\int_{-\beta_i}^{\beta_i}\int_{-\frac{\pi}{2}}^{\frac{\pi}{2}}\frac{D^2+l^2}{D^2}w(\beta,l,\Theta)\cos\Theta$$

$$\left[\frac{2l}{D^2}\frac{\partial}{\partial l}+\frac{D^2+l^2}{D^2}\frac{\partial^2}{\partial l^2}\right]I_i(\beta,l,\Theta)d\Theta d\beta$$

where $w(\beta,l,\Theta)$ is the window function for the sub-domain missed by the circular orbit in the Radon domain, $i=\{1,2\}$ corresponds to arc orbit 1 and arc orbit 2 respectively, and $\beta_i$ determines the arc sub-orbit spanning range.

B. Derivation of the Window Function

Figure 3:
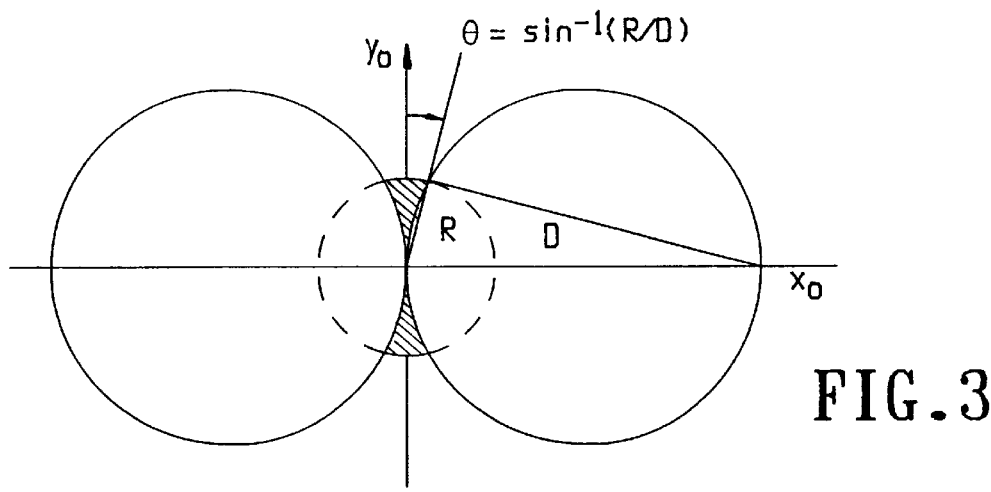
FIG. 3 is a schematic drawing in Radon space showing the inability of the circular orbit alone to satisfy the data sufficiency condition.

By referring to FIG. 3, the section in Radon domain that can not be covered by the radon transform of the circular CB projections is $$\Omega_N=\{\vec{n},\rho)|D(1-\sin^2\theta\sin^2\phi)^{1/2}<|\rho| \quad (B\text{-}1)$$

Actually, we have (see Appendix A)

$$\rho = \frac{Dl}{\sqrt{D^2+l^2}} \quad (B\text{-}2)$$

$$\cos\theta = \frac{D\sin\Theta}{\sqrt{D^2+l^2}} \quad (B\text{-}3)$$

-continued $$\tan\varphi = \frac{D\cos\Theta\cos\beta + l\sin\beta}{-D\cos\Theta\sin\beta + l\cos\beta} \quad \text{(B-4)}$$

Then, from (B-3) we get $$\sin^2\theta = 1 - \cos^2\theta = \frac{D^2\cos^2\Theta + l^2}{D^2 + l^2} \quad \text{(B-5)}$$

and from (B-4) we get $$\sin^2\varphi = \frac{\text{tg}^2\varphi}{1 + \text{tg}^2\varphi} = \frac{(D\cos\Theta\cos\beta + l\sin\beta)^2}{D^2\cos^2\Theta + l^2} \quad \text{(B-6)}$$

Incorporating (B-2), (B-5) and (B-6) in (B-1) we get $$\frac{D|l|}{\sqrt{D^2+l^2}} \rangle D\left[1 - \frac{(D\cos\Theta\cos\beta + l\sin\beta)^2}{D^2+l^2}\right]^{\frac{1}{2}}$$

$$|l| > [D^2+l^2-(D\cos\Theta\cos\beta + l\sin\beta)^2]^{1/2} \quad \text{(B-8)}$$

$$l^2 > D^2+l^2-(D\cos\Theta\cos\beta + l\sin\beta)^2 \quad \text{(B-9)}$$

$$D^2 < (D\cos\Theta\cos\beta + l\sin\beta)^2 \quad \text{(B-10)}$$

Finally, the window function can be written as $$w(\beta, l, \Theta) = \begin{cases} 1 & l\sin\beta > D\cdot(1-\cos\Theta\cos\beta) \\ 1 & l\sin\beta < -D\cdot(1+\cos\Theta\cos\beta) \\ 0 & \text{elsewhere} \end{cases} \quad \text{(B-11)}$$

I claim:

1. A method of imaging an object to form a reconstructed image, the method comprising:
   (a) scanning the object using a source of radiation and a detector of the radiation, the source and the detector being moved around the object to define an orbit comprising (i) a circle orbit for providing a first set of data signals and (ii) a plurality of arc orbits for providing a second set of data signals;
   (b) performing a first reconstruction from the first set of data signals to generate a first reconstruction result;
   (c) performing a second reconstruction from the second set of data signals to generate a second reconstruction result; and
   (d) summing the first reconstruction result and the second reconstruction result to obtain the reconstructed image as a sum of the first reconstruction result and the second reconstruction result.

2. The method of claim 1, wherein the source of radiation is a source of cone-beam radiation.

3. The method of claim 2, wherein the first reconstruction result is a sum of a Feldkamp reconstruction and a complementary term used to correct the Feldkamp reconstruction for use of the cone-beam radiation on the circle.

4. The method of claim 2, wherein the second reconstruction result is generated by summing individual arc reconstruction results for the arc orbits.

5. The method of claim 4, wherein two arc orbits are used.

6. The method of claim 5, wherein, for each of the arc orbits, the individual arc reconstruction result is calculated using a window function to account for a portion of a Radon domain which cannot be covered by a Radon transform of the circle orbit.

7. The method of claim 6, wherein, for any point $\vec{r}$ in the object:
   $(x_L, y_L, z_L)$ is a detector coordinate system which rotates rigidly with the detector;
   $\beta$ is an angle along the arc orbits at which the source is located;
   D is a radius of the arc orbits;
   $\vec{r}$ and a location of the source define a plane which intersects a plane of the detector at a line of intersection, the line of intersection having a point C of closest approach to an origin O of the detector coordinate system such that a line segment connecting O and C has a length l and forms an angle $\Theta$ with a $y_L$ axis of the detector coordinate system; and
   the window function is given by $$w(\beta, l, \Theta) = \begin{cases} 1 & l\sin\beta > D\cdot(1-\cos\Theta\cos\beta) \\ 1 & l\sin\beta < -D\cdot(1+\cos\Theta\cos\beta) \\ 0 & \text{elsewhere}. \end{cases}$$

8. The method of claim 7, wherein:
   (Y,Z) is a projection of $\vec{r}$ onto the detector coordinate system;
   $Y_i$ and $Z_i$ are integration limits determined by dimensions of the detector;
   $\beta_i$ is an integration limit determined by dimensions of the arc orbits;

$$I(\beta, l, \Theta) \equiv \int_{-Z_i}^{Z_i} \int_{-Y_i}^{Y_i} P_{\beta,i}(Y, Z)\delta(Y\sin\Theta + Z\cos\Theta - l)dYdZ;$$

$$P_{a_i}(\beta, l, \Theta) = \frac{D^2+l^2}{D^2} w(\beta, l, \Theta)\cos\Theta\left[\frac{2l}{D^2}\frac{\partial}{\partial l} + \frac{D^2+l^2}{D^2}\frac{\partial^2}{\partial l^2}\right]I_i(\beta, l, \Theta);$$

and the individual arc reconstruction results are given by $$f_{a_i}(\vec{r}) = -\frac{1}{4\pi^2}\int_{-\beta_i}^{\beta_i}\int_{-\frac{\pi}{2}}^{\frac{\pi}{2}} P_{a_i}(\beta, l, \Theta)d\Theta d\beta.$$

9. The method of claim 8, wherein:
   $\omega_0$ is an integration limit determined by a spatial sampling frequency of the detector;
   $L_Z$ is an integration limit along a Z direction;
   $P_\Phi(Y,Z)$ is a cone-beam projection at a point (Y,Z) on the detector;

$$h_\omega(Z) = \int_{-\omega_0}^{\omega_0} |\omega|d\omega\exp(j\omega Z);$$

$$\hat{P}_\Phi(Y, Z) = \frac{D}{(D^2+Y^2+Z^2)^{\frac{1}{2}}} P_\Phi(Y, Z);$$

$$P'_\Phi(Y, Z) = \int_{-\infty}^{\infty} dz\, h_\omega(Z-z)\hat{P}_\Phi(Y, z);$$

the Feldkamp reconstruction is given by $$f_{c_1}(\vec{r}) = \frac{1}{4\pi^2} \oint_{[0,2\pi]} d\Phi \frac{D^2}{(D-\vec{r}\cdot x_L)^2} P'_\Phi(Y(\vec{r}), Z(\vec{r}));$$

$$h_{j\omega}(Y) = \int_{-\omega_0}^{\omega_0} j\omega \exp(j\omega Y) d\omega;$$

$$\sigma_\phi(Y) = \int_{-l_z}^{l_z} \hat{P}_\phi(Y, z) dz;$$

$$P'_\phi(Y) = \frac{\partial}{\partial Y} \sigma_\phi(Y) = \int_{-\infty}^{\infty} h_{j\omega}(Y-y)\sigma_\phi(Y) dy;$$

the complementary term is given by $$f_{c_2}(\vec{r}) = -\frac{1}{4\pi^2} \oint_{[0,2\pi]} d\Phi \frac{y_L}{(D-\vec{r}\cdot x_L)^2} P'_\Phi(Y(\vec{r})); \text{ and}$$

the first reconstruction result is given by $$f_c(\vec{r}) = f_{c_1}(\vec{r}) + f_{c_2}(\vec{r}).$$

10. The method of claim 9, wherein step (b) is performed through a digital signal processing operation which assumes:

$$h_{|\omega|}(n) = \begin{cases} \frac{1}{4} & n = 0 \\ -\frac{1-(-1)^n}{8\pi^2} \frac{1}{n^2} & n \neq 0 \end{cases} \text{ with}$$

and $$h_{j\omega}(n) = \begin{cases} 0 & n = 0 \\ (-1)^n \frac{1}{n} & n \neq 0. \end{cases} \text{ with}$$

11. The method of claim 1, wherein the detector is a flat panel detector.

12. The method of claim 1, wherein at least one of steps (b) and (c) comprises scattering correction.

13. The method of claim 1, wherein the first reconstruction result and the second reconstruction result are both in a filtered backprojection format.

14. The method of claim 1, wherein steps (b)–(d) are performed through parallel cone beam reconstruction.

15. The method of claim 1, wherein the object is longitudinally unbounded, and wherein step (d) comprises providing the reconstructed image as an exact reconstruction of the longitudinally unbounded object.

16. The method of claim 1, wherein step (d) comprises forming a 3D matrix of attenuation coefficient distribution of the object.

17. The method of claim 1, wherein the object is a patient or a region of interest in a patient.

18. The method of claim 1, wherein the reconstructed image is formed for nondestructive testing of the object.

19. The method of claim 1, wherein step (a) comprises performing a quasi-spiral scan of the object.

20. The method of claim 19, wherein the quasi-spiral scan comprises a tilt in plus circle scan.

21. The method of claim 20, wherein the quasi-spiral scan further comprises a tilt out scan.

22. The method of claim 1, wherein the first set of data signals has a higher sampling rate than the second set of data signals.

23. The method of claim 1, further comprising:
(e) locating a volume of interest in the object;
(f) scanning the volume of interest; and
(g) performing steps (b)–(d) again for the volume of interest.

24. The method of claim 23, wherein the detector has a first resolution and a second resolution higher than the first resolution, and wherein the first resolution is used in step (a) and the second resolution is used in step (e).

25. A device for imaging an object to form a reconstructed image, the device comprising:
a source of radiation;
a detector of the radiation;
a gantry for supporting the source and the detector and for moving the source and the detector around the object to define an orbit comprising (i) a circle orbit for providing a first set of data signals and (ii) a plurality of arc orbits for providing a second set of data signals; and
a computing device, receiving the first and second sets of data signals, for (i) performing a first reconstruction from the first set of data signals to generate a first reconstruction result, (ii) performing a second reconstruction from the second set of data signals to generate a second reconstruction result and (iii) summing the first reconstruction result and the second reconstruction result to obtain the reconstructed image as a sum of the first reconstruction result and the second reconstruction result.

26. The device of claim 25, wherein the source of radiation is a source of cone-beam radiation.

27. The device of claim 26, wherein the first reconstruction result is a sum of a Feldkamp reconstruction and a complementary term used to correct the Feldkamp reconstruction for use of the cone-beam radiation on the circle.

28. The device of claim 26, wherein the second reconstruction result is generated by summing individual arc reconstruction results for the arc orbits.

29. The device of claim 28, wherein two arc orbits are used.

30. The device of claim 29, wherein, for each of the arc orbits, the individual arc reconstruction result is calculated using a window function to account for a portion of a Radon domain which cannot be covered by a Radon transform of the circle orbit.

31. The device of claim 30, wherein, for any point $\vec{r}$ in the object:
$(x_L, y_L, z_L)$ is a detector coordinate system which rotates rigidly with the detector;
$\beta$ is an angle along the arc orbits at which the source is located;
D is a radius of the arc orbits;
$\vec{r}$ and a location of the source define a plane which intersects a plane of the detector at a line of intersection, the line of intersection having a point C of closest approach to an origin O of the detector coordinate system such that a line segment connecting O and C has a length l and forms an angle $\Theta$ with a $y_L$ axis of the detector coordinate system; and
the window function is given by $$w(\beta, l, \Theta) = \begin{cases} 1 & l\sin\beta > D\cdot(1-\cos\Theta\cos\beta) \\ 1 & l\sin\beta < -D\cdot(1+\cos\Theta\cos\beta) \\ 0 & \text{elsewhere.} \end{cases}$$

32. The device of claim 31, wherein:

(Y,Z) is a projection of $\vec{r}$ onto the detector coordinate system;

$Y_i$ and $Z_i$ are integration limits determined by dimensions of the detector;

$\beta_i$ is an integration limit determined by dimensions of the arc orbits;

$$I(\beta, l, \Theta) \equiv \int_{-Z_i}^{Z_i} \int_{-Y_i}^{Y_i} P_{\beta,i}(Y, Z)\delta(Y\sin\Theta + Z\cos\Theta - l)dYdZ;$$

$$P_{a_i}(\beta, l, \Theta) = \frac{D^2 + l^2}{D^2} w(\beta, l, \Theta)\cos\Theta \left[\frac{2l}{D^2}\frac{\partial}{\partial l} + \frac{D^2 + l^2}{D^2}\frac{\partial^2}{\partial l^2}\right] I_i(\beta, l, \Theta);$$

and the individual arc reconstruction results are given by $$f_{a_i}(\vec{r}) = -\frac{1}{4\pi^2} \int_{-\beta_i}^{\beta_i} \int_{-\frac{\pi}{2}}^{\frac{\pi}{2}} P_{a_i}(\beta, l, \Theta) d\Theta d\beta.$$

33. The device of claim 32, wherein:

$\omega_0$ is an integration limit determined by a spatial sampling frequency of the detector;

$L_z$ is an integration limit along a Z direction;

$P_\phi(Y,Z)$ is a cone-beam projection at a point (Y,Z) on the detector;

$$h_\omega(Z) = \int_{-\omega_0}^{\omega_0} |\omega| d\omega \exp(j\omega Z);$$

$$\hat{P}_\Phi(Y, Z) = \frac{D}{(D^2 + Y^2 + Z^2)^{\frac{1}{2}}} P_\Phi(Y, Z);$$

$$P'_\Phi(Y, Z) = \int_{-\infty}^{\infty} dz\, h_{|\omega|}(Z - z)\hat{P}_\Phi(Y, z);$$

the Feldkamp reconstruction is given by $$f_{c_1}(\vec{r}) = \frac{1}{4\pi^2} \oint_{[0,2\pi]} d\Phi \frac{D^2}{(D - \vec{r} \cdot x_L)^2} P'_\Phi(Y(\vec{r}), Z(\vec{r}));$$

$$h_{j\omega}(Y) = \int_{-\omega_0}^{\omega_0} j\omega \exp(j\omega Y)d\omega;$$

$$\sigma_\phi(Y) = \int_{-l_z}^{l_z} \hat{P}_\phi(Y, z)dz;$$

-continued $$P'_\phi(Y) = \frac{\partial}{\partial Y}\sigma_\phi(Y) = \int_{-\infty}^{\infty} h_{j\omega}(Y - y)\sigma_\phi(Y)dy;$$

the complementary term is given by $$f_{c_2}(\vec{r}) = -\frac{1}{4\pi^2} \oint_{[0,2\pi]} d\Phi \frac{y_L}{(D - \vec{r} \cdot x_L)^2} P'_\Phi(Y(\vec{r})); \quad \text{and}$$

the first reconstruction result is given by $$f_c(\vec{r}) = f_{c_1}(\vec{r}) + f_{c_2}(\vec{r}).$$

34. The device of claim 33, wherein the computing device generates $f_c(\vec{r})$ through a digital signal processing operation which assumes:

$$h_{|\omega|}(n) = \begin{cases} \dfrac{1}{4} & \text{with } n = 0 \\ -\dfrac{1-(-1)^n}{8\pi^2}\dfrac{1}{n^2} & \text{with } n \neq 0 \end{cases}$$

and $$h_{j\omega}(n) = \begin{cases} 0 & \text{with } n = 0 \\ (-1)^n\dfrac{1}{n} & \text{with } n \neq 0. \end{cases}$$

35. The device of claim 25, wherein the detector comprises a flat-panel detector.

36. The device of claim 35, wherein the flat-panel detector has a frame rate of at least 30 frames per second.

37. The device of claim 35, wherein the flat-panel detector has an image lag of less than 2%.

38. The device of claim 35, wherein the flat-panel detector has a dynamic range of at least 4000:1.

39. The device of claim 35, wherein the flat-panel detector has a size of at least 19.5 cm×24.4 cm.

40. The device of claim 25, further comprising a device for correcting for scatter in the reconstructed image.

41. The device of claim 40, wherein the device for correcting scatter comprises an antiscatter grid disposed between the source and the object.

42. The device of claim 41, wherein the device for correcting scatter further comprises a collimator for collimating the radiation.

* * * * *